United States Patent [19]

Terao et al.

[11] Patent Number: 5,229,385
[45] Date of Patent: Jul. 20, 1993

[54] QUINONE DERIVATIVES, THEIR PRODUCTION AND USE

[75] Inventors: Shinji Terao, Osaka; Kohei Nishikawa, Kyoto, both of Japan

[73] Assignee: Takeda Chemical Industries, Ltd., Osaka, Japan

[21] Appl. No.: 818,856

[22] Filed: Jan. 10, 1992

Related U.S. Application Data

[62] Division of Ser. No. 600,149, Oct. 19, 1990, Pat. No. 5,106,858, which is a division of Ser. No. 343,142, Apr. 25, 1989, Pat. No. 4,985,447, which is a division of Ser. No. 4,138, Jan. 16, 1987, Pat. No. 4,851,413.

[30] Foreign Application Priority Data

Jan. 30, 1986 [JP] Japan ................................. 61-19547
Apr. 23, 1986 [JP] Japan ................................. 61-94168

[51] Int. Cl.$^5$ .................. C07D 277/30; C07D 201/20; A01N 43/78; A61K 31/535
[52] U.S. Cl. ............................. 514/235.5; 514/236.8; 514/326; 514/342; 514/397; 514/399; 544/111; 546/191; 546/208; 546/209; 546/280; 548/204; 548/205; 548/336.1; 548/336.5; 548/341.1; 548/341.5
[58] Field of Search ...................... 548/204, 205, 336.1, 548/336.5, 341.1, 341.5, 191, 208, 209, 280; 514/365, 397, 399, 235.5, 236.8, 326, 342; 546/191, 208, 209, 280; 544/111

[56] References Cited

U.S. PATENT DOCUMENTS 3,929,880 12/1975 Kirchlechner et al. ......... 260/559 A
4,201,588 5/1980 Adin et al. .................... 430/167

(List continued on next page.)

FOREIGN PATENT DOCUMENTS 0003560 8/1979 European Pat. Off. .
0004727 10/1979 European Pat. Off. .
0092136 10/1983 European Pat. Off. .
0171251 2/1986 European Pat. Off. .

OTHER PUBLICATIONS

Hori et al., Chem. Abstracts, vol. 93, No. 25 (1980), p. 810, Abstract No. 238974r.

(List continued on next page.)

*Primary Examiner*—C. Warren Ivy
*Assistant Examiner*—Raymond Covington
*Attorney, Agent, or Firm*—Wenderoth, Lind & Ponack

[57] ABSTRACT

Quinone derivatives represented by the general formula

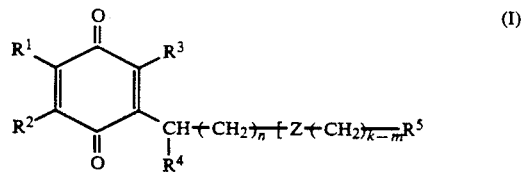

(wherein, $R^1$ and $R^2$, the same or different, refer to hydrogen atom, methyl or methoxymethyl group, or $R^1$ and $R^2$ bind together to form —CH=CH—CH=CH—; $R^3$ is hydrogen atom or methyl group; $R^4$ is nitrogen-containing heterocyclic group which may be substituted; $R^5$ is hydrogen atom, methyl group, hydroxymethyl group which may be substituted, or carboxyl group which may be esterified or amidated; Z is

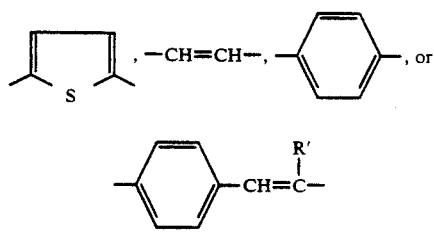

(wherein, R' is hydrogen atom or methyl group); n is an integer from 0 through 12, m is an integer from 0 through 3, and k is an integer from 0 through 7, providing that, when m is 2 or 3, Z and k are able to vary appropriately in the repeating unit shown in []), and the hydroquinone derivatives thereof, are novel compounds, possess improvement effects of metabolism of poly unsaturated fatty acids, particularly two or more of inhibition of production of fatty acid peroxides, inhibition of production of metabolites in 5-lipoxygenase pathway, inhibition of thromboxane $A_2$ synthetase, thromboxane $A_2$ receptor antagonism and scavenging action of active oxygen species, and of use as drugs, such as antithrombotics, anti-vascular constriction agents, anti-asthma agent, antiallergic agents, therpeutics for psoriasis, agents for improvement in heart, brain and cardiovascular systems, therapeutics for nephritis, active oxygen-eliminating agents, anticancer agents, agents for improvement of control of arachidonate cascade products, etc.

11 Claims, No Drawings

U.S. PATENT DOCUMENTS

| | | | |
|---|---|---|---|
| 4,271,083 | 6/1981 | Morimoto et al. | 260/396 R |
| 4,393,075 | 7/1983 | Terao et al. | 424/304 |
| 4,489,096 | 12/1984 | Terao et al. | 424/317 |
| 4,925,855 | 5/1990 | Schermanz et al. | 548/336.1 |
| 4,945,178 | 7/1990 | McCombs | 548/204 |
| 4,999,352 | 3/1991 | Kampe et al. | 548/341.1 |
| 5,023,357 | 6/1991 | Siegel et al. | 548/341.1 |
| 5,100,890 | 3/1992 | Siegel et al. | 548/341.1 |

OTHER PUBLICATIONS

Cameron et al., Aust. J. Chem. (1976), vol. 29, pp. 1163–1165.

Kort et al., J. Chem. Soc. (C) 1966) pp. 2190–2196.

Furukawa et al., Chem. Abstr. vol. 84, No. 11 (1976) Abstract No. 74280x.

Babichev et al., Chem. Abstr., vol. 70, No. 25, p. 339, Abstract No. 115062j (1976).

Takada et al., Chem. Abstr., vol. 75, No. 9 (1971) p. 432 Abstract No. 63546b.

Cameron et al., Journ. Chem. Soc. (C) 1969, pp. 1245–1251.

QUINONE DERIVATIVES, THEIR PRODUCTION AND USE

This application is a division of application Ser. No. 07/600,149, filed Oct. 19, 1990 (now U.S. Pat. No. 5,106,858) which is a division of Ser. No. 07/343,142, filed Apr. 25, 1989 (now U.S. Pat. No. 4,985,447) which is a division of application Ser. No. 07/004,138, filed Jan. 16, 1987 (now U.S. Pat. No. 4,851,413).

This invention relates to novel quinone derivatives each of which exerts two or more effects among thromboxane $A_2$ synthetase inhibition, thromboxane $A_2$ receptor antagonism, 5-lipoxygenase inhibition and scavenging action of active oxygen species, and is usuful, based on the composite effects, for treatment and prevention of diseases due to dysfunction of heart, brain, lung and kidney. This invention also relates to the method of production of the said quinone derivatives, and pharmaceutical compositions containing such derivatives. This invention is useful in the field of medicine.

PRIOR ART

A number of reports have been published on specific inhibitors, antagonists, or scavengers for one of thromboxane $A_2$ (hereinafter abbreviated as $TXA_2$) synthetase, $TXA_2$ receptor, 5-lipoxygenase and active oxygen species. However, no attempt has been made to design a compound having a composite pharmacological action consisting of two or more effects among $TXA_2$ synthetase inhibition, $TXA_2$ receptor antagonism, 5-lipoxygenase inhibition and scavenging action of active oxygen species.

This invention offers novel quinone compounds exerting two or more effects among $TXA_2$ synthetase inhibition, $TXA_2$ receptor antagonism, 5-lipoxygenase inhibition, and scavenging action of active oxygen species.

This invention relates to

1. Quinone derivatives represented by the general formula

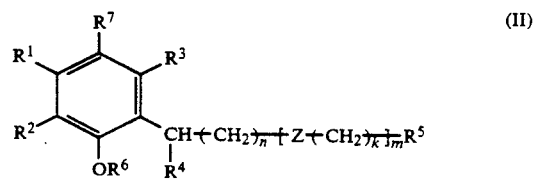

(wherein, $R^1$ and $R^2$ which are, the same or different, refer to a hydrogen atom, methyl or methoxy group, or $R^1$ and $R^2$ bind together to form $-CH=CH-CH=CH-$; $R^3$ is a hydrogen atom or methyl group; $R^4$ is a nitrogen-containing heterocyclic group which may be substituted; $R^5$ is a hydrogen atom, methyl group, hydroxymethyl group which may be substituted, or carboxyl group which may be esterified or amidated; Z is

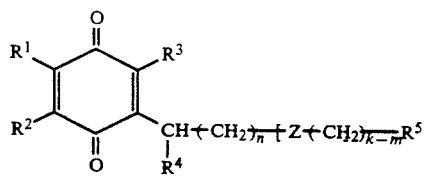

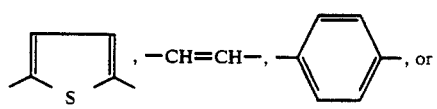

(wherein, R' is a hydrogen atom or methyl group); n is an integer from 0 through 12, m is an integer from 0 through 3, and k is an integer from 0 through 7, providing that, when m is 2 or 3, Z and k are able to vary appropriately in the repeating unit shown in []), and the hydroquinone derivatives thereof, 2. a method of production of quinone derivatives represented by the general formula (I) characterized by the reaction of a compound represented by the general formula

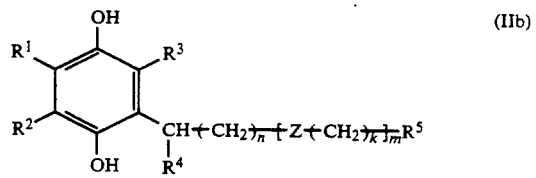

(wherein, $R^1$, $R^2$, $R^3$, $R^4$, $R^5$, Z, k, m and n are the same as described above; $R^6$ is a hydrogen atom, methyl, methoxymethyl, benzyl, or 2-tetrahydropyranyl group; $R^7$ is a hydrogen atom, hydroxyl, methoxy, methoxymethyloxy, benzyloxy, or 2-tetrahydropyranyloxy group) with an oxidant, 3. a method of production of hydroquinone derivatives represented by the general formula

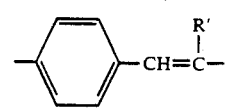

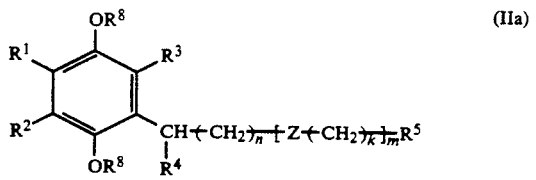

(wherein, the symbols are the same as described above) characterized by the protective-group eliminating reaction of a compound having the general formula (wherein, $R^1$, $R^2$, $R^3$, $R^4$, $R^5$, Z, k, m, and n are the same as described above; $R^8$ is methyl, methoxymethyl, benzyl, or 2-tetrahydropyranyl), and, 4. pharmaceutical compositions containing, as the active ingredient, a quinone derivative represented by the general formula (I) or a hydroquinone derivative thereof.

The nitrogen-containing heterocyclic groups represented by $R^4$ in the general formula (I) described above include 5- or 6-membered cyclic groups containing at least one nitrogen atom as the ring member atom, in the concrete, pyridyl groups (2-pyridyl, 3-pyridyl, 4-pyridyl), thiazolyl (2-thiazolyl, 4-thiazolyl, 5-thiazolyl), imidazolyl (1-imidazolyl, 2-imidazolyl, 4-imidazolyl, 5-thiazolyl and 1-imidazolyl are preferable, and 3-pyridyl is the most desirable. These nitrogen-containing heterocyclic groups may contain 1 to 3 substituents at a given position on the ring, and such substituents include alkyl groups having 1 to 3 carbon atoms such as methyl and ethyl, phenyl group, p-tolyl group, m-tolyl group, pyridyl group (2-pyridyl, 3-pyridyl), and 3-pyridylmethyl group.

The hydroxymethyl group represented by $R^5$ may be substituted, including, in addition to the unsubstituted hydroxymethyl group, methoxymethyl, acetoxymethyl, nitroxymethyl, and carbamoyloxymethyl; the esterified carboxyl group includes alkoxycarbonyl groups having 2 to 5 carbons such as methoxycarbonyl, ethoxycarbonyl, propoxycarbonyl, and butoxycarbonyl. The amidated carboxyl group represented by $R^5$ may be a substituted aminocarbonyl in which the amino group is substituted, or a cyclic aminocarbonyl. The substituents for the amino group in the substituted aminocarbonyl include alkyl having 1 to 4 carbon atoms such as methyl, ethyl, propyl and butyl, aryl having 6 to 10 carbon atoms such as phenyl and naphthyl (which may be substituted by hydroxyl, amino, nitro, halogen, methyl or methoxy at a given position of the ring), and the hydroxyl group; the amidated carboxyl groups are exemplified by aminocarbonyl, mono- or di-alkylaminocarbonyl having 2 to 4 carbon atoms (methylaminocarbonyl, ethylaminocarbonyl, isopropylaminocarbonyl, dimethylaminocarbonyl), phenylaminocarbonyl, substituted phenylaminocarbonyl (p-hydroxyphenylaminocarbonyl), p-methoxyphenylaminocarbonyl, m-chlorophenylaminocarbonyl), diphenylaminocarbonyl, hydroxyaminocarbonyl, N-hydroxy-N-methylaminocarbonyl, and N-hydroxy-N-phenylaminocarbonyl. The cyclic aminocabonyl includes morpholinocarbonyl and piperidinocarbonyl.

The quinone compounds represented by the general formula (I) and the hydroquinone derivatives thereof (IIb) may be the salts of inorganic acids such as hydrochloric acid, nitric acid, and phosphoric acid, or of organic acids such as methanesulfonic acid, toluenesulfonic acid, benzenesulfonic acid, and succinic acid.

The compounds represented by the general formula (I) of this invention are able to be produced by the reaction of a compound represented by the general formula (II) with an oxidant.

The kind of the oxidant used and the conditions of the oxidation of a compound represented by the general formula (II) vary according to the species of $R^6$ and $R^7$.

The compounds in which $R^6$ and $R^7$ are hydrogen atoms in the general formula (II), i.e. phenol compounds, are able to be easily converted into quinone compounds (I) by using a Fremy's salt as the oxidant. The amount of the Fremy's salt used is 2 to 4 moles per 1 mole of the compound (II), the solvent being preferably methanol, acetonitrile, ethanol, dioxane, 1,2-dimethoxyethane, or a aqueous solvent thereof. The reaction temperature is 10°–80° C. and the reaction time is usually about 2–10 hours.

The compounds in which $R^6$ is a hydrogen atom and $R^7$ is a hydroxyl group in the general formula (II), i.e. hydroquinone compounds, are able to be easily converted into quinone compounds (I) by using a mild oxidant such as air, oxygen, a Fremy's salt, ferric chloride, ferric sulfate, hydrogen peroxide and a peracid. Such reactions are usually conducted in the presence of a solvent, and such solvents include methanol, acetonitrile, dioxane, 1,2-dimethoxyehtane and aqueous solvents consisting of the said organic solvents and water. When air or oxygen is used as the oxidant, the reaction is carried out at a neutral or weakly alkaline pH (pH 7.0–pH9.0). A buffer solution (e.g. phosphate buffer) is used to maintain the pH. The reaction temperature is $-10°$ C. to $30°$ C., and the reaction time is usually within 2 hours. When the oxidant used is ferric chloride, ferric sulfate or a Fremy's salt, the amount of the oxidant used is preferably about 1 to 2 moles per 1 mole of the compound (II). The reaction temperature is $-10°$ C. to $30°$ C., and the reaction time is usually within 1 hour.

The compound (II) in which $R^6$ is methyl, methoxymethyl, benzyl, or 2-tetrahydropyranyl group, and $R^7$ is methoxy, methoxymethyloxy, benzyloxy, or 2-tetrahydropyranyloxy group, i.e. hydroquinone diether compounds, are able to be easily converted into quinone compounds (I) by using silver oxide (AgO) or cerium-(IV) ammonium nitrate (hereinafter abbreviated as CAN) as the oxidant. When silver oxide (AgO) is used the reaction is conducted in water or a aqueous organic solvent (e.g. dioxane, acetonitrile) in the presence of nitric acid at $-10°$ C. to $30°$ C. When CAN is used as the oxidant, the reaction is conducted in a aqueous organic solvent (e.g. acetonitrile, methanol), especially aqueous acetonitrile, in the presence of CAN alone or CAN together with pyridine-2,6-dicarboxylic acid N-oxide, pyridine-2,4,6-tricarboxylic acid or pyridine-2,6-dicarboxylic acid or the like. The suitable mixing ratio of CAN and the pyridine carboxylic acid described above is usually about 1:1 (molar equivalent). The reaction temperature is about $-5°$ C. to about $30°$ C.

The compounds in which $R^5$ is carbamoyloxymethyl, hydroxyaminocarbonyl, N-substituted hydroxyaminocarbonyl, hydroxymethyl, carboxyl, alkoxycarbonyl, aminocarbonyl, or substituted aminocarbonyl group are derived from the compounds in which $R^5$ is hydroxymethyl, carboxyl, alkoxycarbonyl, or acyloxymethyl group by the per se known reactions described below.

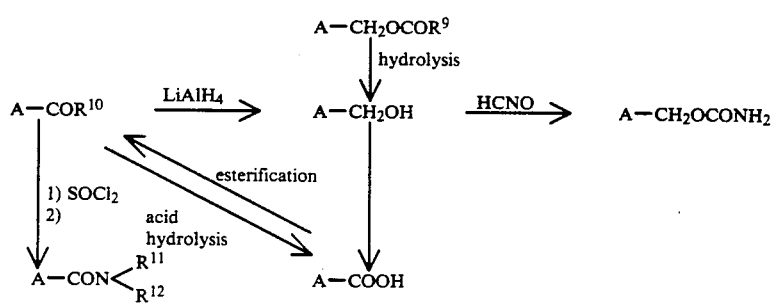

[wherein, A is
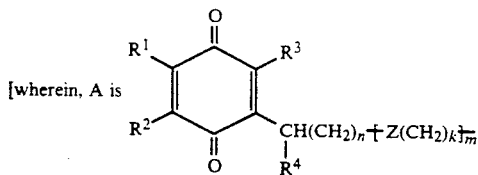

(wherein $R^1$, $R^2$, $R^3$, $R^4$, n, m, k, and Z are the same as described above); $R^9$ and $R^{10}$ are $C_{1-3}$ alkyl groups (e.g. methyl, ethyl, propyl); and $R^{11}$ and $R^{12}$ are hydrogen atoms, $C_{1-7}$ lower alkyl groups (e.g. methyl, ethyl, propyl, i-propyl, butyl, pentyl, hexyl) or aryl groups (e.g. phenyl, naphthyl)].

The hydroquinone compounds represented by the general formula (IIb) are able to be produced by protective group removing reaction (acid hydrolysis) of a compound represented by the general formula (IIa). When $R^8$ is a methyl group in the general formula (IIa), the acid catalyst is preferably hydrogen bromide and the solvent is preferably acetic acid or water. The reaction temperature is 60° C.–120° C., preferably about 80° C. When $R^8$ is a methoxymethyl group or 2-tetrahydropyranyloxy group in the general formula (IIa), the acid catalyst used is an organic or inorganic acid such as sulfuric acid, methanesulfonic acid, p-toluenesulfonic acid, and camphorsulfonic acid, and the solvent is methanol, ethanol, or an aqueous organic solvent (e.g. methanol, acetone, tetrahydrofuran, ether, acetonitrile). The reaction temperature is 20°–80° C., preferably 50°–60° C.

When $R^8$ is a benzyl group, the compounds (IIb) are able to be produced by catalytic reduction by a usual method of a compound (IIa) in the presence of a catalyst such as palladium-carbon.

The compounds in which, in the general formula (I), n is 0, Z is —CH=CH—, k is an integer from 0 through 7, and m is 1, or the compounds in which n is an integer from 4 through 11 and m is 0, that is, the compounds represented by the following formula

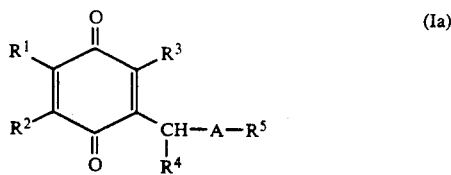

[wherein, $R^1$, $R^2$, $R^3$, $R^4$, and $R^5$ are the same as described above, A refers to the formula $-(CH_2)_{k'+4}$ (wherein k' is an integer from 0 through 5) or A-$R^5$ refers to the formula $-CH=CH-(CH_2)_{k'+2}-R^5$ (wherein k' and $R^5$ are the same as described above)] are able to be produced by sulfur eliminating reduction of a compound represented by the general formula

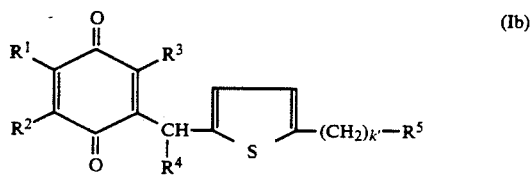

(wherein, the symbols are the same as described above), followed by oxidation of the products.

The sulfur eliminating reduction of a compound represented by the general formula (Ib) is conducted by using Raney nickel. The reaction is conducted in a solvent such as methanol, ethanol and ethyl acetate, in the presence of about 10 to 20 times by weight of Raney nickel when hydrogen gas is not used, and at a temperature in the range from the room temperature to 100° C. Five to 10 times by weight of Raney nickel is used when hydrogen gas is present and a pressure of 5–200 atm is applied. The compounds produced by the sulfur eliminating reduction are hydroquinone derivatives, and therefore are converted into quinone compounds (Ia) by oxidation with ferric chloride or air as required.

The quinone compounds (I) and the hydroquinone derivatives thereof (IIb) thus produced are able to be isolated by the per se known methods for isolation and purification (e.g. chromatography, crystallization).

The quinone compounds (I) and the hydroquinone derivatives thereof (IIb) of this invention can be converted from one to the other by chemical or biochemical oxidation or reduction of the quinone nucleus or the hydroquinone nucleus of the compounds. In general, hydroquinone derivatives (IIb) are susceptible to oxidation with oxygen, air or the like, and therefore usually treated as the corresponding stable quinone compounds (I). Because hydroquinone compounds (IIb) and quinone compounds (I) are easily converted from one to the other by chemical or biochemical oxidation-reduction, the quinone compounds (I) and the hydroquinone derivatives (IIb) are considered to have equivalent properties when the compounds exert their pharmaceutical actions under physiological conditions.

The quinone compounds (I) are able to be easily converted into the hydroquinone compounds (IIb) by a per se known method using a mild reductant such as sodium hydrosulfite, sodium hydrogen sulfite and sodium borohydride, or by catalytic reduction in the presence of platinum oxide, or palladium-carbon.

Some quinone compounds (I) and (IIb) have structurally an asymmetric center at the alpha ($\alpha$) carbon on the side chain of the quinone or hydroquinone nucleus, and such compounds are optically active. This implies that the compounds (I) and (IIb) of this invention include optically active compounds as well as racemic compounds.

Each of the compound (I) and (IIb) of this invention exert improvement effect of metabolism of polycarboxylic unsaturated fatty acids (linoleic acid, $\gamma$-linolenic acid, $\alpha$-linolenic acid, arachidonic acid, dihomo-$\gamma$-linolenic acid, eicosapentaenoic acid), among the effect particularly two or more of inhibition of production of fatty acid peroxide (antioxidation), inhibition of production of metabolites by 5-lipoxygenase system (e.g. leucotrienes, 5-hydroxyeicosatetraenoic acid, 5-peroxyeicosatetraenoic acid, lipoxines), inhibition of thromboxane $A_2$ synthetase, thoromboxane $A_2$ receptor antagonism, and scavenging action of active oxygen species, and have very little toxicity and very few side effects. Therefore the compounds (I) and (IIb) are expected to be useful for treatment and prevention of diseases in mammals (mouse, rat, rabbit, dog, monkey, human, etc.), such as thrombosis, ischemic diseases (e.g. myocardial infarction, cerebral stroke) due to contraction or twitch of arterial smooth muscle in heart, lung, brain and kidney, nephritis, pulmonary failure, bronchial asthma, psoriasis, inflammation, immediate allergy, arteriosclerosis, atherosclerosis, fatty liver, hepatitis, cirrhosis of the liver, hypersensitivity pneumonitis, immunodeficiency, diseases of cardiovascular system (myocardial infarction, cerebral stroke, nephritis, etc.) due to disorder of tissues, enzymes, and cells caused by active oxygen species (superoxides, hydroxide radicals, lipid peroxides, etc.), and cancer, being useful as medicines such as antithrombotics, anti-vascular constriction agents, anti-asthma agent, antiallergic agents, therapeutics for psoriasis, agents for improvement of heart, brain and cardiovascular system, therapeutics for nephritis, active oxygen-eliminating agents, anticancer agents, agents for improvement of control of arachidonate cascade products, etc.

Because the compounds of this invention have low toxicity, the compounds as they are or as pharmaceutical compositions produced by mixing with a per se known, pharmaceutically acceptable carrier or excipient or the like [e.g. tablets, capsules (including soft capsules and microcapsules), liquid preparations, injections, suppositories] are able to be given safely orally or parenterally. The dose varies according to the subjects to be treated, the route of administration, symptoms, etc. For example, when given orally to an adult patient with thrombosis, the unit dose is usually about 0.1 mg/kg-20 mg/kg body weight, preferably about 0.2 mg/kg-10 mg/kg body weight which is desirably given about 1-3 times a day.

The compounds (II) are able to be produced by one of the following methods.

The compounds represented by the general formula (IIb) described above are able to be produced by condensation of a hydroquinone compound represented by the general formula

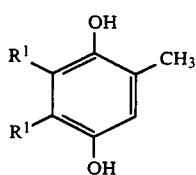

(wherein, $R^1$ is the same as described above) with a compound represented by the general formula

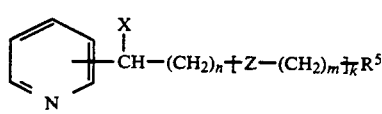

(wherein, k, m, n, $R^5$ and Z are the same as described above, and X is hydroxyl or acetoxy group) in the presence of an acidic catalyst. The said acidic condensation is carried out without solvent or in an organic solvent, in the presence of concentrated sulfuric acid, trifluoromethylsulfonic acid, or fluorosulfonic acid in the atmosphere of nitrogen or argon gas. The reaction solvents include methylene chloride, 1,2-dichloroethane, benzene, and toluene. The reaction temperature is 30°-100° C., preferably 60°-90° C. The amount of the catalyst is 1.2-5 mole equivalents, preferably 2-3 times moles.

Among the compounds represented by the general formula (II), the compounds in which $R^6$ is methyl and $R^7$ is methoxy group are able to be synthesized, for example, by the procedure described below.

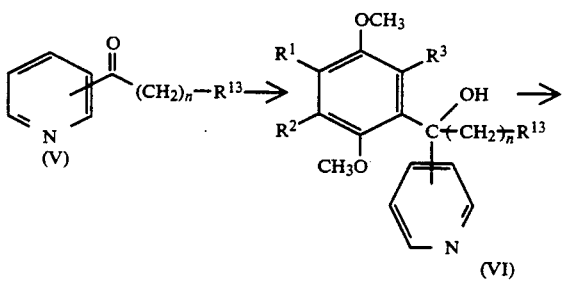

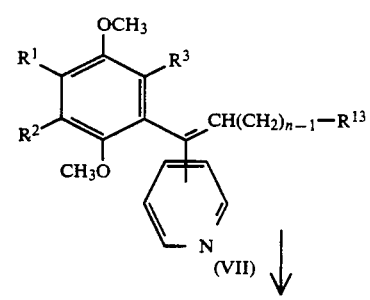

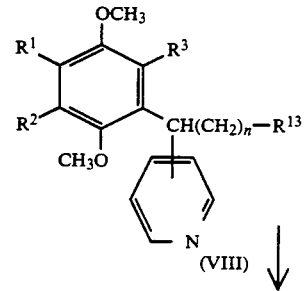

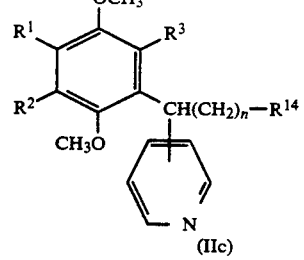

(wherein, $R^1$, $R^2$, $R^3$ and n are the same as described above; $R^{13}$ is a hydrogen atom, methyl group or hydroxyl group which may be substituted; $R^{14}$ is a hydrogen atom, methyl group, hydroxyl group which may be substituted, or carboxyl group which may be substituted).

That is, an intermediate (VI) is able to be produced by the reaction of a pyridylketone derivative (V) with a compound represented by the general formula

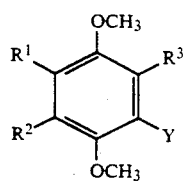

(wherein, $R^1$, $R^2$, and $R^3$ are the same as described above, and Y is Li or MgBr). This condensation can be carried out in anhydrous diethyl ether or anhydrous tetrahydrofuran, in the atmosphere of nitrogen or argon at $-80°\text{-}20°$ C. Dehydration proceeds when the said intermediate (VI) is allowed to react in the presence of an acid catalyst (e.g. concentrated sulfuric acid, p-toluenesulfonic acid) in an organic solvent (e.g. acetic acid, methylene chloride, 1,2-dichloroethane) at $10°\text{-}100°$ C. for 1-3 hours, to give an olefin compound (VII). The said olefin compound (VII) is subjected to catalytic reduction in an organic solvent (e.g. acetic acid, ethanol, ethyl acetate) in the presence of a catalyst (e.g. palladium-carbon, palladium black), to give a compound (VIII). The compound (VIII) is able to be converted into a carboxylic acid derivative (IIc) by a routine method.

Among the compounds represented by the general formula (II), the compounds represented by the following formulas (IId and IIe) are able to be produced also by the following procedure.

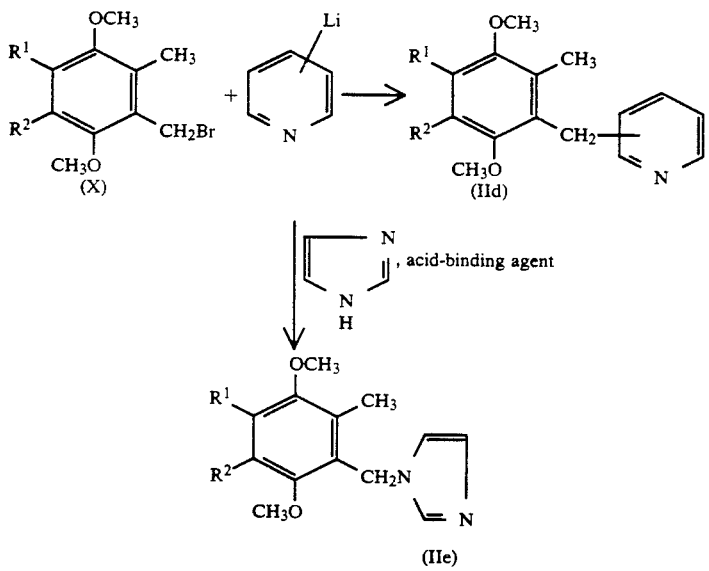

(wherein, $R^1$ and $R^2$ are the same as described above).

That is, reaction of the bromide derivative (X) with 2-, 3-, or 4-pyridyl lithium in an anhydrous solvent (e.g. tetrahydrofuran, diethyl ether) in the atmosphere of an inert gas (e.g. nitrogen gas, argon, helium), to give a compound (IId). The imidazolyl derivative (IIe) is able to be produced by the reaction of the bromide derivative (X) with imidazole in the presence of an acid-binding agent (e.g. triethylamine, sodium hydride) in dimethylformamide or dimethylsulfoxide.

The novel quinone derivatives of this invention are effective in improvement of metabolism of polyunsaturated fatty acids, particularly control of biosynthesis of arachidonate cascade products (inhibition of 5-lipoxygenase, inhibition of $TXA_2$ synthetase, $TXA_2$ receptor antagonism) and active oxygen species elimination, and useful as medicines for improvement of dysfunction and circulatory systems in heart, brain, lung and kidney, as antiasthma agents, as antiallergic agents, etc.

EXAMPLE 1

Compound No. 1

To a solution of 4.0 g (32.5 mmol) of 1- (3-pyridyl)ethanol in 25 ml of dichloroethane, 4.96 g (32.6 mmol) of 2,3,5-trimethylhydroquinone and 4.5 ml (50.9 mmol) of trifluoromethanesulfonic acid were added and refluxed by heating for 20 hours in argon atomosphere. After cooling, ice water was added, washed with ethyl acetate to eliminate neutral substances, and made weakly alkaline with a saturated solution of sodium hydrogen carbonate. The resultant substance was extracted with ethyl acetate, and the extract was washed with water, dried, oxidized with air and concentrated under reduced pressure. The residue was purified with silica gel column chromatography (isopropyl ether-ethyl acetate (1:2)), to give 5.1 g of 3,5,6-trimethyl-2-[1-(3-pyridyl)ethyl]-1,4-benzoquinone (yield 61%). Physical data of this compound are shown in Table 1.

EXAMPLE 2

Compound No. 2 to a solution of 1.0 g (5.4 mmol) of phenyl-(3-pyridyl)methanol and 823 mg (5.4 mmol) of 2,3,5-trimethylhydroquinone in 15 ml of dichloroethane, 0.5 ml (9.4 mmol) of concentrated sulfuric acid was added, and refluxed by heating for 2 hours. The reaction mixture was made weakly alkaline with a saturated aqueous solution of sodium hydrogen carbonate, from which the organic phase was separated while the aqueous phase was extracted with chloroform and the extract was combined with the organic phase. The organic phase was washed with water, dried, and oxidized with air, from which the solvent was evaporated off. The residue was purified with silica gel column chromatography (isopropyl ether-ethyl acetate (1:1)), to give 1.25 g (72.7%) of 3,5,6-trimethyl-2-[phenyl-(3-pyridyl)methyl]-1,4-benzoquinone. The physical data are shown in Table 1.

EXAMPLE 3

Compound No. 3

To a solution of 1.0 g (3.36 mmol) of ethyl 4-[hydroxy-(3-pyridyl)]methyl-α-methylcinnamate in 10 ml of dichloroethane, 514 mg (3.38 mmol) of 2,3,5-trimethylhydroquinone and 0.28 ml (5.26 mmol) of concentrated sulfuric acid were added and refluxed by heating for 2 hours. The reaction mixture was made weakly alkaline with a saturated solution of sodium hydrogen carbonate, and the organic phase was separated while the aqueous phase was extracted with chloroform and the extract was combined with the organic phase. The organic phase was oxidized with ferric chloride, washed with water, dried, and concentrated. The residue was purified with silica gel column chromatography (isopropyl ether-acetic ester (1:1)), to give 1.2 g (yield 82.7%) of ethyl 4-[3,5,6-trimethyl-1,4-benzoquinon -2-yl(3-pyridyl)methyl]-α-methylcinnamate. The physical data are shown in Table 1.

EXAMPLE 4

Compound No. 4

4-[3,5,6-trimethyl-1,4-benzoquinon-2-yl-(3-pyridyl)-methyl]-α-methylcinnamic acid, 0.7 g (1.75 mmol), was hydrogenated with 0.2 g of 5% Pd-carbon in 6 ml of acetic acid (the reaction completed in about 2 hours). The catalyst was filtered off, and the filtrate was concentrated, to which water was added and neutralized with a saturated aqueous solution of sodium hydrogen carbonate. The resultant substance was extracted with ethyl acetate, and oxidized by shaking with an aqueous solution of ferric chloride. After the organic phase was washed with water and dried, the solvent was evaporated off and the residue was purified with silica gel column chromatography (ethyl acetate-ethanol (9:1)) and recrystallized from ethyl acetate, to give 0.3 g (44.2%) of 3-(4-[3,5,6-trimethyl-1,4-benzoquinon-2-yl-(3-pyridyl)methyl]phenyl)propionic acid. The physical data are shown in Table 1.

In a similar way, Compound No. 13 and Compound No. 16 were prepared. The physical data are shown in Table 2-1.

EXAMPLE 5

Compound No. 5

Ethyl 4-[3,5,6-trimethyl-1,4-benzoquinon-2-yl-(3-pyridyl)methyl]-α-methylcinnamate, 1.2 g (2.8 mmol), was dissolved in 20 ml of concentrated hydrochloric acid, and refluxed by heating for 2 hours. After cooling, the reaction mixture was neutralized with a saturated aqueous solution of sodium hydrogen carbonate, and the resulting substance was extracted with ethyl acetate. The extract was washed with water and dried, and the solvent was evaporated off. The residue was purified with silica gel column chromatography (ethyl acetate-ethanol(9:1)), and recrystallized from ethyl acetate, to give 0.96 g (85.6%) of 4-[3,5,6-trimethyl-1,4-benzoquinon-2-yl(3-pyridyl)methyl]-α-methylcinnamic acid. The physical data are shown in Table 1.

EXAMPLE 6

Compound No. 6

The solution of 400 mg (1.12 mmol) of 5-(2,5-dimethoxy-3,4,6-trimethylphenyl)-5-(3-pyridyl)pentanoic acid in 8 ml of acetonitrile-water (1:1) was cooled to 0° C., to which the solution of 1.55 g (2.82 mmol) of cerium ammonium nitrate in 6 ml of acetonitrile-water (1:1) was added with stirring. The reaction mixture was stirred for 30 minutes, neutralized with sodium hydrogen carbonate, and extracted with ethyl acetate. The extract was washed with water and dried, and the solvent was evaporated off. The residue was purified with silica gel column (ethyl acetate), and recrystallized from ethanol, to give 200 mg (54.3%) of 5-(3,5,6-trimethyl-1,4-benzoquinon -2-yl)-5-(3-pyridyl)pentanoic acid.

According to the methods described in the Example, Compounds No. 7 to No. 15, Compounds No. 19 and No. 21 were prepared. The data of these compounds are shown in Table 2-1 or Table 2-2.

EXAMPLE 7

Compound No. 16

To a solution of 1.1 g (3.09 mmol) of 1-(3,6-dimethoxy-2,4,5-trimethylphenyl)-1-(3-pyridyl)heptane in 20 ml of acetonitrile-water (1:1), the solution of 4.5 g (8.2 mmol) of cerium ammonium nitrate (CAN) in 15 ml of acetonitrile-water was added dropwise with stirring at 0° C. and stirred for 30 minutes after the completion of addition. The reaction product was isolated by a routine method, to give 635 mg (63%) of 1-(3,5,6-trimethyl-1,4-benzoquinon -2-yl)-1-(3-pyridyl)heptane. The physical data are shown in Table 2-1.

EXAMPLE 8

Compound No. 17

3,5,6-trimethyl-2-[1-(3-pyridyl)ethyl]-1,4-benzoquinone hydrochloride

To a solution of 5.4 g (21.2 mmol) of 3,5,6-trimethyl-2-[1-(3-pyridyl)ethyl]-1,4-benzoquinone in ethanol (30 ml), 1.8 ml of concentrated hydrochloric acid was added and the resultant solution was concentrated under reduced pressure. To the residue ethyl acetate was added and the resultant crystals were collected by filtration and recrystallized from ethanol-ethyl acetate, to give 5.6 g (91%) of 3,5,6-trimethyl-2-[1-(3-pyridyl)ethyl]-1,4-benzoquinone hydrochloride.

According to the method described in the Example, Compound No. 18 and Compound No. 24 were prepared from Compound No. 14 and Compound No. 23, respectively.

Physical data are shown in Table 2-1.

EXAMPLE 9

Compound No. 13

7-(3-pyridyl)-7-(3,5,6-trimethyl-1,4-benzoquinon -2-yl)-6-heptenoic acid (2.5 g) was hydrogenated in the presence of 5% palladium-carbon (0.5 g) in acetic acid (20 ml) (the reaction completed in about 2 hours). The catalyst was removed, the solvent was concentrated, and water (10 ml) and methanol (40 ml) were added. This solution was neutralized by addition of a saturated solution of sodium hydrogen carbonate, and the hydroquinone derivative was oxidized by aeration. After completion of oxidation, the mixture was concentrated under reduced pressure and the product was extracted with chloroform. The organic phase was dried with magnesium sulfate and concentrated under reduced pressure. The residue was dissolved in ethyl acetate and purified with silica gel column chromatography [ethyl acetate-ethanol(9:1)] and recrystallized from a mixture of ethyl acetate-isopropyl ether, to give 7-(3-pyridyl)-7-(3,5,6-trimethyl-1,4-benzoquinon -2-yl)heptanoic acid (2.1 g).

According to the method described in the Example 9, Compound No. 16 was synthesized from 1-(3-pyridyl)-1-(3,5,6-trimethyl-1,4-benzoquinon -2-yl)-1-heptane. Physical properties and nuclear magnetic resonance spectrum are shown in Table 2-1.

EXAMPLE 10

Compound No. 22

A solution of 0.6 g (2.3 mmol) of 1-(2,5-dimethoxy-3,4,6-trimethylbenzyl)imidazole in 8 ml of acetonitrile-water (1:1) was cooled to 0° C., to which a solution of 3.1 g (5.64 mmol) of cerium ammonium nitrate in 5 ml of acetonitrile-water (1:1) was added with stirring. The reaction mixture was stirred for 30 minutes, made weakly alkaline with an aqueous solution of sodium hydrogen carbonate, and extracted with ethyl acetate. The extract was washed with water and dried, and the solvent was evaporated off. The residue was purified with silica gel column chromatography (ethyl acetate). The eluate from the column was concentrated, to which ethanol was added and then 0.2 ml of concentrated hydrochloric acid was added. The solution was concentrated and the resulting crystals were collected by filtration, to give 0.3 g (48.9%) of 2-[(1-imidazolyl)methyl]-3,5,6-trimethyl-1,4-benzoquinone hydrochloride.

Physical properties and nuclear magnetic resonance spectrum of this compound are shown in Table 2-3.

EXAMPLE 11 compound No. 23

The mixture of 3.6 g (17.9 mmol) of (3-pyridyl)-(2-thienyl)methanol, 2.74 g (18.0 mmol) of 2,3,5-trimethylhydroquinone and 2.3 ml of methanesulfonic acid, and 45 ml of dichloroethane was stirred at 60° C. for 2 hours.

After cooling, an aqueous solution of sodium hydrogen carbonate was added to the reaction mixtrue, the organic phase was separated and the water phase was extracted with chloroform. The extract was added to the organic phase, shake with 50 ml of the aqueous solution of 5.8 g (21. 5 mmol) of ferric chloride, and made weakly alkaline with an aqueous solution of sodium hydrogen carbonate, from which the organic phase was separated. The organic phase was washed with water, dried, concentrated, and purified with silica gel column chromatography (ethyl acetate), to give 6.0 g (92.3%) of 2-[(3-pyridyl)(2-thienyl)methyl]-3,5,6-trimethyl-1,4-benzoquinone.

Physical properties and nuclear magnetic resonance spectrum of the compound described above are shown in Table 2-3.

EXAMPLE 12

Another Method for Production Compound No. 7

The solution of 1.2 g (3.7 mmol) of 2-[(3-pyridyl)(2-thienyl)methyl]-3,5,6-trimethyl-1,4-benzoquinone in 20 ml of ethanol was refluxed by heating in the presence of 24 g of Raney nickel (W-6) for 5 hours. After cooling the catalyst was removed by filtration, and the filtrate was concentrated and redissolved in ethyl acetate and shaken with the solution of 1.2 g of ferric chloride in 10 ml of water. The mixture was made weakly alkaline with sodium hydrogen carbonate, from which the organic layer was separated, washed with water, dried, and concentrated. The residue was purified with silica gel column chromatography (ethyl acetate-isopropyl ether (1:1)), to give 0.8 g (72.5%) of 2-[1-(3-pyridyl)pentyl]-3,5,6-trimethyl-1,4-benzoquinone (Compound No. 7).

EXAMPLE 13

7-(2,5-dimethoxy-3,4,6-trimethylphenyl)-7-(3-pyridyl)heptanoic acid (1.0 g, 2.6 mmol) prepared in the Reference Example 11 was dissolved in 47% aqueous hydrogen bromide (5 ml) and the solution was heated at a reflux temperature for 2 hours. After the reaction was completed, the reaction mixture was cooled. The solution was made alkaline with sodium bicarbonate and the product was extracted with ethylacetate. The extract was washed with water, dried, and evaporated in vacuo. The resulting hydroquinone was oxidized with air and the solvent was evaporated to yield 7-(3,5,6-trimethyl-1,4-benzoquinon-2-yl)-7-(3-pyridyl)heptanoic acid (0.8 g, 86.8%) after crystallization from ethylacetate, m.p. 126°–127° C.

8-(3,5,6-trimethyl-1,4-benzoquinon-2-yl)-8-(3-pyridyl)octanoic acid, m.p. 113°–114° C. was prepared from 8-(2,5-dimethoxy-3,4,6-trimethylphenyl)-8-(3-pyridyl)octanoic acid by a similar procedure of the above example.

TABLE 1

| Compound No. | Prepared by the procedure of Example | Molecular formula physical properties m.p. | Nuclear magnetic resonance spectrum, δ value (ppm) in CDCl$_3$, TMS as internal standard |
|---|---|---|---|
| 1 | 1 | C$_{16}$H$_{17}$NO$_2$ oil | 1.63(3H, d, J=3.0Hz), 1.97(3H, s), 2.00(6H, s), 4.50(1H, quartet, J=6Hz), 7.27(1H, dd, J=7.5 & 4.5Hz), 7.67(1H, dt, J=7.5 & 1.5Hz), 8.45 (1H, dd, J=4.5 & 1.5Hz), 8.47(1H, d, J=1.5Hz) |
| 2 | 2 | C$_{21}$H$_{19}$NO$_2$ oil | 1.90(3H, s), 1.97(3H, s), 2.02(3H, s), 5.90(1H, s), 7.05–7.35(6H, m), 7.50(1H, dt, J=4.5 & 1.5Hz), 8.45 (2H, m) |
| 3 | 3 | C$_{27}$H$_{27}$NO$_4$ oil | 1.30(3H, t, J=7.0Hz), 1.92(6H, s), 1.97(3H, s), 2.03(3H, s), 2.10(3H, d, J=1.5Hz), 4.25(2H, q, J=7.0Hz), 5.90(1H, s), 7.17(2H, ABd, J=7.5 Hz), 7.37(2H, ABd, J=7.5Hz), 7.50 (1H, dt, J=7.5 & 1.5Hz), 7.67(1H, m), 8.47(1H, d, J=1.5Hz), 8.50(1H, dd, J=4.5 & 1.5Hz) |
| 4 | 4 | C$_{24}$H$_{23}$NO$_4$ 205–207° C. | in dimethylsulfoxide-d$_6$: 1.33(3H, s), 1.90(3H, s), 1.93(3H, d, J=1.0Hz), 2.50(2H, m), 2.70(2H, m), 5.80(1H, s), 7.03(2H, d, J=7.5 Hz), 7.18, 2H, d, J=7.5Hz), 7.27 (1H, dd, J=7.5 & 4.5Hz), 7.50(1H, dt, J=7.5 & 1.5Hz), 8.37(2H, m) |
| 5 | 5 | C$_{25}$H$_{23}$NO$_4$ 199–201° C. | 2.03(6H, s), 2.13(3H, d, J=1.0Hz), 5.90(1H, s), 7.17(2H, d, J=7.5Hz), 7.30(1H, dd, J=7.5 & 4.5Hz), 7.40 (2H, d, J=7.5Hz), 7.60(1H, dt, J= 7.5 & 1.5Hz), 7.77(1H, s), 8.47(1H, d, J=1.5Hz), 8.57(1H, dd, J=4.5 & 1.5Hz), 10.40(1H, broad s) |
| 6 | 6 | C$_{19}$H$_{21}$NO$_4$ 82–84° C. | 1.60(2H, m), 1.93(3H, s), 1.97(3H, s), 2.10(2H, s), 2.25(2H, m), 2.33 (2H, t, J=6.8Hz), 4.30(1H, t, J= 7.5Hz), 7.27(1H, dd, J=7.5 & 4.5 Hz), 7.75(1H, dt, J=7.5 & 1.5Hz), 7.80(1H, broad s), 8.43(1H, dd, J= 4.5 & 1.5Hz), 8.53(1H, d, J=1.5Hz) |

TABLE 2-1

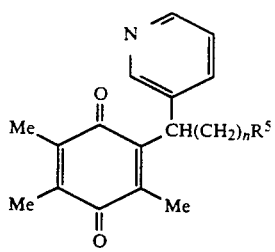

| Compound No. | n | R⁵ | Prepared by the procedure of Example | Molecular formula physical properties m.p. | Nuclear magnetic resonance spectrum, δ value (ppm) in CDCl₃, TMS as internal standard |
|---|---|---|---|---|---|
| 7 | 4 | H | 6, 12 | C₁₉H₂₃NO₂ oil | 0.87(3H, t, J=6Hz), 1.30(4H, m), 1.93(3H, s), 2.00(3H, s), 2.10(3H, s), 2.20(2H, m), 4.23(1H, t, J=7.5Hz), 7.20(1H, dd, J=7.5&4.5Hz), 7.70(1H, dt, J=7.5&1.5Hz), 8.40(1H, dd, J=4.5&1.5Hz), 8.47(1H, d, J=1.5Hz) |
| 8 | 3 | CH₂OH | 6 | C₁₉H₂₃NO₃ 104–105° C. | 1.10–1.80(4H, m), 1.93(3H, s), 1.97(3H, s), 2.08(3H, s), 2.00–2.40(2H, m), 3.60(2H, t, J=6.0Hz), 4.23(1H, t, J=7.5Hz), 7.23(1H, dd, J=7.5&4.5Hz), 7.70(1H, dt, J=7.5&1.5Hz), 8.37(1H, dd, J=4.5&1.5Hz), 8.47(1H, d, J=1.5Hz) |
| 9 | 3 | CH₂OCO–Me | 6 | C₂₁H₂₅NO₄ oil | 1.20–1.80(4H, m), 1.97(3H, s), 2.00(3H, s), 2.03(3H, s), 2.13(3H, s), 2.00–2.40(2H, m), 4.06(2H, t, J=6.8Hz), 4.27(1H, t, J=7.5Hz), 7.27(1H, dd, J=7.5&4.5Hz), 7.75(1H, dt, J=7.5&1.5Hz), 8.47(1H, dd, J=4.5&1.5Hz), 8.53(1H, d, J=1.5Hz) |
| 10 | 4 | COOH | 6 | C₂₀H₂₃NO₄ 68–69° C. | 1.10–1.80(4H, m), 1.97(3H, s), 2.00(3H, s), 2.13(3H, s), 1.90–2.40(2H, m), 2.33(2H, t, J=6.8Hz), 4.23(1H, t, J=7.5Hz), 7.27(1H, dd, J=7.5&4.5Hz), 7.77(1H, dt, J=7.5&1.5Hz), 8.50(1H, dd, J=4.5&1.5Hz), 8.53(1H, d, J=1.5Hz), 8.80(1H, broad s) |
| 11 | 4 | CH₂OH | 6 | C₂₀H₂₅NO₃ oil | 1.20–1.70(6H, m), 1.97(3H, s), 2.00(3H, s), 2.13(3H, s), 2.00–2.40(2H, m), 3.60(2H, t, J=6.0Hz), 4.27(1H, t, J=7.5Hz), 7.25(1H, dd, J=7.5&4.5Hz), 7.75(1H, dt, J=7.5&1.5Hz), 8.47(1H, dd, J=4.5Hz&1.5Hz), 8.53(1H, d, J=1.5Hz) |
| 12 | 4 | CH₂OCO–Me | 6 | C₂₂H₂₇NO₄ 60–61° C. | 1.10–1.80(6H, m), 1.97(3H, s), 2.00(3H, s), 2.03(3H, s), 2.13(3H, s), 1.80–2.30(2H, m), 4.03(2H, t, J=6.0Hz), 4.23(2H, t, J=7.5Hz), 7.23(1H, dd, J=7.5&4.5Hz), 7.73(H, dt, J=7.5&1.5Hz), 8.47(1H, dd, J=4.5&1.5Hz), 8.53(1H, d, J=1.5Hz) |
| 13 | 5 | COOH | 6, 9, 12 | C₂₁H₂₅NO₄ 126–127° C. | 1.10–1.80(6H, m), 1.93(3H, s), 1.98(3H, s), 2.13(3H, s), 1.90–2.40(2H, m), 2.30(2H, t, J=6.8Hz), 4.23(1H, t, J=7.5Hz), 7.27(1H, dd, J=7.5&4.5Hz), 7.80(1H, dt, J=7.5&1.5Hz), 8.47(1H, dd, J=4.5&1.5Hz), 8.53(1H, d, J=1.5Hz), 9.85(1H, br) |
| 14 | 0 | H | 6 | C₁₅H₁₅NO₂ 66–67° C. | 2.03(6H, s), 2.10(3H, s), 3.87(2H, s), 7.20(1H, dd, J=4.5&7.5Hz), 7.53(1H, dt, J=7.5&1.5Hz), 8.47(1H, dd, J=4.5&1.5Hz), 8.52(1H, d, J=1.5Hz) |
| 15 | 2 | H | 6 | C₁₇H₁₉NO₂ 56–57° C. | 0.93(3H, t, J=7.5Hz), 1.97(3H, s), 2.00(3H, s), 2.10(6H, s), 2.27(2H, q, J=7.5Hz), 4.17(1H, t, J=7.5Hz), 7.23(1H, dd, J=7.5&4.5Hz), 7.70(1H, dt, J=7.5&1.5Hz), 8.40(1H, dd, J=4.5&1.5Hz), 8.47(1H, d, J=1.5Hz) |
| 16 | 6 | H | 4, 7, 9 | C₂₁H₂₇NO₂ 44–45° C. | 0.87(3H, t, J=6.0Hz), 1.30(10H, m), 1.95(3H, s), 2.00(3H, s), 2.10(3H, s), 4.23(1H, t, J=7.5Hz), 7.18(1H, dd, J=7.5&4.5Hz), 7.70(1H, dt, J=7.5&1.5Hz), 8.40(1H, dd, J=4.5&1.5Hz), 8.48(1H, d, J=1.5Hz) |
| 17 | 1 | H hydrochloride | 8 | C₁₆H₁₈NO₂Cl 188–191° C. | 1.73(3H, d, J=7.5Hz), 1.90(3H, s), 2.03(3H, s), 2.20(3H, s), 4.48(1H, q, J=7.5Hz), 7.93(1H, dd, J=7.5&4.5Hz), 8.40(1H, d, J=4.5Hz), 8.67(1H, s), 8.70(1H, d, J=4.5Hz) |
| 18 | 0 | H hydrochloride | 8 | C₁₅H₁₆NO₂Cl 164–167° C. | 2.00(3H, s), 2.03(3H, s), 4.10(2H, s), 7.92(1H, dd, J=7.5&4.5Hz), 8.36(1H, d, J=4.5Hz), 8.70(1H, s), 8.75(1H, d, J=4.5Hz) |

TABLE 2-2

| Compound No. | Formula | Prepared by the procedure of Example | Molecular formula physical properties m.p. | Nuclear magnetic resonance spectrum, δ value (ppm) in CDCl$_3$, TMS as internal standard |
|---|---|---|---|---|
| 19 | 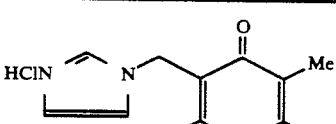 | 6 | C$_{17}$H$_{13}$NO$_2$<br>102–103° C. | 2.27(3H, s), 4.00(2H, s), 7.17(1H, dd, J=7.5&4.5Hz), 7.57(1H, dt, J=7.5&1.5Hz), 7.68(2H, m), 8.07(2H, m), 8.43(1H, dd, J=4.5&1.5Hz), 8.53(1H, d, J=1.5Hz) |
| 20 | | 1 | C$_{24}$H$_{21}$NO$_4$<br>232–233° C. | (DMSO-d$_6$)<br>1.88(6H, s), 1.95(3H, d, J=1.0Hz), 6.87(1H, s), 6.47(1H, d, J=16.0Hz), 7.15(2H, d, J=7.5Hz), 7.30(1H, dd, J=7.5&4.5Hz), 7.52(2H, d, J=7.5Hz), 7.53(1H, dt, J=7.5&1.5Hz), 7.57(1H, d, J=16.0Hz), 8.40(1H, d, J=1.5Hz), 8.43(1H, dd, J=4.5&1.5Hz), 12.30(1H,) |
| 21 | | 1 | C$_{16}$H$_{17}$NO$_2$<br>122–123° C. | 1.60(3H, d, J=3.80Hz), 1.98(6H, s), 2.03(3H, s), 4.50(1H, q, J=3.80Hz), 7.18(2H, A$_2$B$_2$), 8.53(2H, A$_2$B$_2$) |

TABLE 2-3

| Compound No. | Formula | Prepared by the procedure of Example | Molecular formula physical properties m.p. | Nuclear magnetic resonance spectrum, δ value (ppm) in CDCl$_3$, TMS as internal standard |
|---|---|---|---|---|
| 22 | 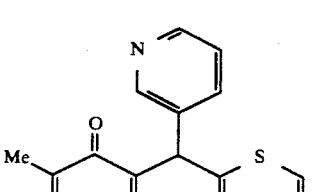 | 10 | C$_{13}$H$_{15}$N$_2$ClO$_2$<br>225–228° C. | 2.03(6H, s), 2.37(3H, s), 5.53(1H, s), 7.27(1H, t, J=1.5Hz), 7.37(1H, t, J=1.5Hz), 9.80(1H, t, J=1.5Hz) |
| 23 | | 11 | C$_{19}$H$_{17}$NO$_2$S<br>oil | 2.00(6H, s), 2.03(3H, s), 6.08(1H, s), 6.83(1H, dd, J=4.5&1.5Hz), 6.95(1H, dd, J=5.5&4.5Hz), 7.20(1H, dd, J=7.5&4.5Hz), 7.25(1H, dd, J=5.5&1.5Hz), 7.57(1H, dt, J=7.5&1.5Hz), 8.47(2H, m) |

TABLE 2-3-continued

| Compound No. | Formula | Prepared by the procedure of Example | Molecular formula physical properties m.p. | Nuclear magnetic resonance spectrum, δ value (ppm) in CDCl₃, TMS as internal standard |
|---|---|---|---|---|
| 24 | 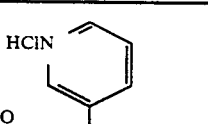 | 8 | C₁₉H₁₈NClO₂S 185–188° C. decomp. | 1.95(3H, s), 2.05(3H, s), 2.22(3H, s), 6.00(1H, s), 7.03(2H, m), 7.37(1H, dd, J=4.5&1.5Hz), 7.83(1H, dd, J=7.5&4.5Hz), 8.27(1H, broad d, J=7.5Hz), 8.57(1H, broad s), 8.67(1H, broad d, J=4.5Hz) |
| 25 | 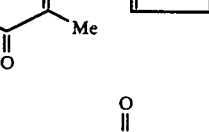 | 6, 8 | C₁₅H₁₆HClO₄ 152–153° C. | 2.18(3H, broad s), 3.98(3H, s), 4.02(3H, s), 4.07(2H, broad s), 7.93(1H, dd, J=7.5&4.5Hz), 8.40(1H, broad d, J=7.5Hz), 8.77(2H, m) |

EXAMPLE 14

Example of Pharmaceutical Composition

A) Capsules

| | |
|---|---|
| (1) Compound No. 1 | 50 mg |
| (2) Very fine powder of cellulose | 30 mg |
| (3) Lactose | 37 mg |
| (4) Magnesium stearate | 3 mg |
| total | 120 mg |

(1), (2), (3) and (4) were mixed and filled in gelatin capsules.

B) Soft capsules

| | |
|---|---|
| (1) Compound No. 17 | 50 mg |
| (2) Corn oil | 100 mg |
| total | 150 mg |

According to a routine method, (1) and (2) were mixed and filled in soft capsules.

C) Tablets

| | |
|---|---|
| (1) Compound No. 18 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethylcellulose | 20 mg |
| total | 120 mg |

According to a routine method, these were mixed and compressed by tablet machine.

EXPERIMENT 1

Inhibition of 5-lipoxygenase $10^7$ RBL-1 cells (rat basophilic leukemia cells) were suspended in 0.5 ml of MCM (mast cell medium). To the suspension was subsequently added a solution consisting of 0.5 ml of MCM, 50 μg of arachidonic acid, 10 μg of A-23187 (calcium ionophore, Eli Lilly), and a solution of a quinone compound in ethanol at the final concentration of 1 μM, 0.1 μM, 0.01 μM or 0.001 μM of the test compound was added and allowed to react at 37° C. for 20 minutes. After the reaction, 4 ml of ethanol containing 1,4-dimethoxy-2-methyl-3-(3-methoxypropyl)-naphthalene as an internal standard were added, mixed well by shaking, and kept at room temperature for 10 minutes. Then the mixture was centrifuged for 10 minutes (2000 rpm), and the supernatant was separated. The supernatant was concentrated to dryness under reduced pressure. To the concentrate, 0.5 ml of 60 % aqueous methanol was added. One hundred μl of this solution was subjected to high performance liquid chromatography for quantitative analysis of 5-HETE (5-hydroxyeicosatetraenoic acid). The amount of 5-HETE was analyzed by measurement of the absorbance at 273 nm with a UV absorption monitor.

Inhibitory effect (IE) of production of 5-HETE is expressed by $(1-b/a) \times 100$, wherein a is the peak hight or the area corrected with the peak due to the internal standard in the absence of the quinone compound, and b is the peak hight or peak area corrected with the peak due to the internal standard in the presence of the quinone compound.

The results proved to be the potent inhibition of production of 5-HETE, as shown in Table 5.

EXPERIMENT 2

Inhibition of Thromboxane A₂ (TXA₂) Synthetase

As a preparation of TXA₂ synthetase, horse platelet microsome treated with indomethacin (indomethacin-treated horse platelet microsome: IPM) according to the method of Needleman et al. (Science 193 163, 1979) was used. To 60 μl of the solution of IPM in 50 mM Tris buffer(pH 7.5) (containing 140 μg on the protein basis), 60 μl of a solution containing a drug at a variable concentration was added and kept still at room temperature for 5 minutes. One hundred μl of this mixture was taken, to which 20 μl of a buffer containing 30 ng of prostaglandin H₂ (PGH₂) with ice-cooling and kept still at 0° C. for 5 minutes to produce thromboxane A₂ (TXA₂). The reaction was stopped by addition of 500 μl of Tris buffer, and 50 μl of the resultant solution was subjected to radioimmunoassay of thromboxane $B_2$ ($TXG_2$), a stable metabolite of $TXA_2$ [Shibouta et al. Biochem. Pharmacol. 28 3601, 1979]. The rate of inhibition (%) of $TXA_2$ synthetase was determined from the difference in $TXB_2$ productivity between the untreated group and the treated group.

In the following the results of the experiment with some representative compounds are shown in Table 3.

EXPERIMENT 3

Inhibition of Production of Lipid Peroxide in Rat Brain Homogenate

Procedure: Sprague-Dawley rats (male, 9-15 weeks old) anesthetized with pentobarbital (50 mg/kg, intraperitoneal administration) were venesected and the brain tissue was resected. The tissue was homogenized in phosphate buffer (pH 7.4), and used as a 5% homogenate (on weight basis). The brain homogenate was allowed to react at 37° C. for 1 hour, and the amount of lipid peroxide produced was determined with the thiobarbituric acid method according to the method of Okawa et al.(Analytical Biochem 95 551, 1979). The drug was added to the 5% homogenate before the reaction at 37° C. for 1 hour so that the final concentration might be $5 \times 10^{-7}$ or $10^{-6}$M. Inhibition of production of lipid peroxide was expressed as the rate of inhibition in % of the amount produced in the solvent(DMSO)-treated group.

The results are shown in Table 3.

TABLE 3

| Compound No. | Inhibition of production of 5-HETE (%) | | Inhibition of Thromboxane $A_2$ ($TXA_2$) synthetase (%) | | Inhibition of production of lipid peroxide in rat brain homogenate (%) | |
|---|---|---|---|---|---|---|
| | $10^{-7M}$ | $10^{-6M}$ | $10^{-7M}$ | $10^{-6M}$ | $5 \times 10^{-7M}$ | $10^{-6M}$ |
| 1 | 46 | 84 | 37 | 76 | 6 | 90 |
| 2 | 60 | 85 | 45 | 89 | 32 | 100 |
| 5 | 28 | 73 | 7 | 65 | 29 | 100 |
| 7 | 35 | 86 | — | 32 | 26 | 100 |
| 8 | 63 | 88 | 6 | 37 | 20 | 100 |
| 9 | 62 | 90 | 18 | 54 | 17 | 100 |
| 10 | 52 | 90 | 24 | 67 | 13 | 100 |
| 11 | 61 | 88 | 13 | 67 | 15 | 100 |
| 12 | 67 | 91 | 22 | 56 | 15 | 100 |
| 13 | 16 | 64 | 48 | 87 | 20 | 84 |
| 14 | 80 | 92 | 35 | 61 | 46 | 100 |
| 15 | 57 | 91 | 15 | 76 | 52 | 100 |
| 16 | 77 | 96 | 6 | 49 | 44 | 100 |

EXPERIMENT 4

Effect on Occurrence of Ventricular Arrhythmia Due to Ischemia-reperfusion in Rat Procedure: The experiment was carried out in Sprague-Dawley rat (male, 11-12 weeks old) according to the method of A. S. Manning (Cir.Res. 55, 545, 1984). A rat was given orally a drug or water at the dose of 5 ml/kg, and anesthetized 1 hour later with pentobarbital (50 mg/kg, intraperitoneal injection). The rat was thoractomized under artificial respiration and the coronary left anterior descending artery was ligated for 5 minutes, followed by reperfusion for 10 minutes. The incidences of ventricular tachycardia, ventricular fibrillation and cardiac arrest observed for the 10 minutes of reperfusion were determined.

The results are shown in Table 4. Compound No. 1, when given orally at the dose of 30 mg/kg, inhibited significantly the incidences of ventricular tachycardia, ventricular fibrillation and cardiac arrest.

TABLE 4

Effect on the occurrence of ventricular arrhythmia due to ischemia-reperfusion in rat

| Group | Dose mg/kg. p.o. | Ventricular tachycardia | Ventricular fibrillation | Cardiac arrest |
|---|---|---|---|---|
| Control group | — | 18/18 | 17/18 | 11/18 |
| Compound No. 1 | 30 | 6/8* | 3/8** | 1/8* |

:The denominator is the number of rats used and the numerator is the number of rats showing abnormal cardiac function.
:Significance test: $X^2$ test,
*$p < 0.05$,
**$p < 0.01$

EXPERIMENT 5

Effect on Cerebral Ischemic Seijure in Spontaneously Hypertensive Rat

Procedure: A spontaneously hypertensive rat (male, 20-23 weeks old) was given orally a compound or water at the dose of 5 ml/kg, and 1 hour later anesthetized with pentobarbital. Bilateral common carotid arteries were ligated, and the interval from immediately after the ligation to the occurrence of seijure (cramp, jumping, etc.) was measured.

The results are shown in Table 5. Compound No. 1 given orally at 30 mg/kg prolonged remarkably the interval to the occurrence of cerebral ischemic seijure. The said compound exerts protective effects against cerebral ischemia.

TABLE 5

Effects on cerebral ischemic seijure in rat

| Group | Dose mg/kg, p.o. | Interval till occurrence of ischemic siejure (min) |
|---|---|---|
| Control group | — | 122 ± 20 |
| Compound No. 1 | 30 | 385** ± 33 |

Each group consisted of 5 cases.
Student's t-test:
**$p < 0.01$

EXPERIMENT 6

Proteinuria Improving Effect in Rat with Adriamycin-induced Nephrosis

Procedure: The experiment was carried out with Sprague-Dawley rat (male, 5 weeks old) according to the method of T. Bertani et al. [(Laboratory Invest. 46, 16, (1982)]. Adriamycin was given intravenously at the dose of 7.5 mg/kg and two weeks later urine was collected for 24 hours after water was loaded orally at 10 ml/kg. Total urinary protein and albumin excreted in the urine were determined; rats of which total urinary protein was 20 mg/100 g/24 hours or more were chosen for the experiment. The control group received water (vehicle) alone at 10 ml/kg/day, and the Compound No. 18 group received the Compound at the dose of 50 mg/kg/day (10 ml/kg, water) once a day for 2 weeks. After 1 week or 2 weeks of treatment with the drug, 24 hour-urine was collected to deter mine total urinary protein and albumin. Two weeks later blood was taken from the thoracic aorta of the rat under pentobarbital anesthesia (50 mg/kg, intraperitoneal injection) to determine plasma cholesterol level.

The results are shown in Table 6. The total urinary protein in the control group increased after two weeks of treatment as compared with the pretreatment value, and urinary albumin increased both after 1 week and after 2 weeks of treatment as compared with the pretreatment value. In Compound No. 18 group, neither total urinary protein nor urinary albumin differed from the respective pretreatment values. Furthermore, the serum cholesterol level after 2 weeks was decreased remarkably by the treatment with Compound No. 18. These results prove that the Compound No. 18 improves adriamycin-induced nephrosis.

TABLE 6

| Improving effect on adriamycin-induced nephrosis in rat | | | |
|---|---|---|---|
| | Before treatment | 1 week after | 2 weeks after |
| control (10 ml/kg/day water, p.o., n = 7) | | | |
| total urinary protein (mg/100 g/24 hr) | 72 ± 28 | 70 ± 17 | 87 ± 24* |
| urinary albumin | 23 ± 10 | 37 ± 12* | 51 ± 17** |
| serum cholesterol (mg/dl) | — | — | 131 ± 39 |
| Compound No. 18 (50 mg/kg/day, p.o., n = 3) | | | |
| total urinary protein (mg/100 g/24 hr) | 76 ± 28 | 55 ± 17 | 59 ± 9 |
| urinary albumin | 28 ± 14 | 25 ± 10 | 31 ± 7 |
| serum cholesterol (mg/dl) | — | — | 49 ± 4# |

Paired t-test against pretreatment value
*p < 0.05,
**p < 0.01
Student's t-test against the control value
p < 0.05

EXPERIMENT 7

Improving Effect on Glomerulonephritis in Rat

Procedure: Nephritic rat was prepared according to the method of Matsunaga et al. [Folia pharmacol. japon. 78, 491, (1981)] using Sprague-Dawley rat (male, 5 weeks old). That is, the rat was immunized preliminarily by subcutaneous injection of a mixture of 3 mg of rabbit serum albumin (RSA) and an equal volume of Freund's complete adjuvant, and from two weeks after the RSA was given intravenously at the dose of 1 mg/rat three times a week for 8 weeks. Then 24 hour-urine was collected to determine total urinary protein and urinary albumin. Rats of which total urinary protein was 20 mg/100 g/24 hr or more were chosen for the experiment. The control group received water (vehicle) alone at 10 ml/kg/day, and the Compound No. 18 group received the Compound at the dose of 50 mg/kg/day (10 ml/kg, water) once a day for 2 weeks. After 1 week and 2 weeks of treatment, 24 hour-urine was collected to determine total urinary protein and urinary albumin.

The results are shown in Table 7. As compared with the control group, the Compound No. 18 group showed decreased total urinary protein and urinary albumin. These results prove that the Compound No. 18 improves nephritis.

TABLE 7

| Improving effect on glomerulonephritis in rat | | | |
|---|---|---|---|
| | Before treatment | 1 week after | 2 weeks after |
| control group (water, 10 ml/kg/day, p.o., n = 3) | | | |

TABLE 7-continued

| Improving effect on glomerulonephritis in rat | | | |
|---|---|---|---|
| | Before treatment | 1 week after | 2 weeks after |
| total urinary protein (mg/100 g/24 hr) | 65 ± 21 | 60 ± 20 | 74 ± 9 |
| urinary albumin | 33 ± 15 | 31 ± 15 | 33 ± 7 |
| Compound No. 18 group (50 mg/kg/day, p.o., n = 4) | | | |
| total urinary protein (mg/100 g/24 hr) | 75 ± 28 | 37 ± 8* | 48 ± 16* |
| urinary albumin | 45 ± 21 | 17 ± 5* | 24 ± 12* |

Paired t-test against pretreatment value, *p < 0.05

EXPERIMENT 8

Thromboxane $A_2$ ($TXA_2$) Receptor Antagonism

Procedure: A spiral strip of the rabbit aorta (2-3 mm wide, about 3 cm long) was suspended in Krebs-Henseleit solution under the load of 2 g. The Krebs-Henseleit solution was saturated with a mixed gas of 95%$O_2$-5%$CO_2$ and warmed at 37° C. Inhibition of the contraction of the vascular strip caused by a $TXA_2$ mimic substance, U-46619* ($10^{-7}$M), by pretreatment with Compound No. 13 30 minutes before was studied.

The results are shown in Table 8

The Compound No. 13 inhibited the vascular contraction caused by U-46619 by 14% at $10^{-6}$M, and by 86% at $10^{-5}$M, thus exerting a remarkable $TXA_2$ receptor antagonism.

TABLE 8

| Thromboxane $A_2$ receptor antagonism | | | |
|---|---|---|---|
| drug | concentration (M) | No. of cases | Inhibition of contraction of rabbit aorta strip due to U-46619($10^{-7}$M) (% inhibition) |
| Compound No. 13 | $10^{-6}$ | 6 | 14 ± 4 |
| Compound No. 13 | $10^{-5}$ | 6 | 86 ± 8 | mean ± standard error
*U-46619:(5Z,9α,11α,13E,15S)-15-hydroxy-9,11-(epoxymethano)prosta-5,13-diene-1-acid (manufactured by Upjohn Co., U.S.A.)

EXPERIMENT 9

Toxicological Study in the Rat

Procedure:

Five weeks old, male Wistar rats were used. The rats were given the Compound 18 orally once a day for 14 days at doses of 100 and 300 mg/kg/10 ml of water as a suspension with 5% gum arabic. Control rats were given vehicle (10 ml/kg of water) alone. After fasting a night following the final dose of a 2 week treatment, the rats were anesthetized with ethyl ether and the blood was collected into a heparinized syringe from the abdominal aorta and the plasma was separated for the examination of blood chemistry. Blood parameters such as total protein, glucose, calcium, urea nitrogen, creatinine, total cholesterol, total bilirubin, alkaline phosphatase (ALP), leucine aminopeptidase (LAP), lactate dehydrogenase (LDH), glutamic oxaloacetic transaminase (GOT), glutamic pyruvic transaminase (GPT), creatine phosphokinase (CPK), albumin and A/G ratio were analysed by use of auto-analyzer (Hitachi 716). The organs such as liver, kidney, heart, lung, spleen, adrenal glands, thymus, testris, brain and hypophysis were excised and weighed. Some organs (liver, kidney, heart, lung, spleen) were fixed in 10% neutral formalin solution for histological examinations. Bone marrow was fixed as well without weighing. These fixed organs were stained with Hematoxyline-Eosin for histological examinations.

Results:

The rats that received the Compound 18 (300 mg/kg) tended to have a lower body weight, but the change was not significant (Table 9). Both doses (100 and 300 mg/kg) produced no significant changes in any organ weight (Table 9) and produced no changes in the blood chemistry (Table 10). In the group of 300 mg/kg of the Compound 18, one of 5 rats showed a mild splenomegaly and increased extramedullary hematopoiesis. The other organs showed no changes (Table 11).

REFERENCE EXAMPLE 1

A solution of 10.0 g (63.3 mmol) of 3-bromopyridine in 100 ml of ether was cooled to −78° C., to which 40 ml (64 mmol) of 1.6M n-butyllithium hexane solution was added dropwise with stirring. After completion of the addition, the mixture was stirred for further 15 minutes, to which the solution of 5.45 g (63.3 mmol) of γ-butyrolactone in 15 ml of ether was added dropwise, and stirred for further 1 hour at −78° C.-room temperature. To the reaction mixture an aqueous solution of ammonium chloride, and the resultant substance was extracted with ethyl acetate. The extract was washed

TABLE 9

Body and organ weights of rats treated with Compound 18 for 2 weeks

| | | B.V. (g) | Liver (g) | Kidney (g) | Heart (g) | Lung (g) | Spleen (g) | Thymus (mg) | Adrenals (mg) | Thyroid (mg) | Hypophy. (mg) | Gonads (g) | Brain (g) |
|---|---|---|---|---|---|---|---|---|---|---|---|---|---|
| Control | Mean | 176.1 | 6.684 | 1.749 | 0.774 | 0.949 | 0.694 | 0.478 | 46.2 | 13.9 | 9.0 | 1.930 | 1.789 |
| | SE | 3.8 | 0.166 | 0.033 | 0.017 | 0.038 | 0.032 | 0.024 | 1.1 | 0.7 | 0.2 | 0.059 | 0.020 |
| Compound 18 100 mg/kg | Mean | 170.3 | 6.347 | 1.579 | 0.709 | 0.872 | 0.673 | 0.450 | 47.7 | 11.4 | 8.3 | 1.906 | 1.747 |
| | SE | 4.2 | 0.222 | 0.106 | 0.023 | 0.025 | 0.030 | 0.032 | 2.8 | 1.4 | 1.0 | 0.029 | 0.016 |
| Compound 18 300 mg/kg | Mean | 162.0 | 6.264 | 1.508 | 0.913 | 0.929 | 0.703 | 0.447 | 43.0 | 12.0 | 8.1 | 1.873 | 1.714 |
| | SE | 8.3 | 0.138 | 0.069 | 0.194 | 0.035 | 0.061 | 0.028 | 1.8 | 1.0 | 0.4 | 0.060 | 0.040 |

TABLE 10

Blood chemistry-Group menn values (mean ± S.D.)

| Group Compound Dose (mg/kg/day) | | 1 Control — | | 2 Compound 18 100 | | 3 Compound 18 300 | |
|---|---|---|---|---|---|---|---|

| Group | Number of animals | Total protein (g %) | Glucose (mg %) | Calcium (mg %) | Urea nitrogen (mg %) | Greatinine (mg %) | Total cholesterol (mg %) | Total bilirubin (mg %) |
|---|---|---|---|---|---|---|---|---|
| 1M | 5 | 5.52 ± 0.12 | 102 ± 7 | 10.02 ± 0.28 | 15.7 ± 1.1 | 0.5 ± 0.1 | 51 ± 4 | 0.32 ± 0.04 |
| 2M | 4 | 5.51 ± 0.11 | 104 ± 11 | 9.84 ± 0.41 | 15.8 ± 0.7 | 0.5 ± 0.0 | 47 ± 7 | 0.27 ± 0.03 |
| 3M | 5 | 5.48 ± 0.20 | 97 ± 11 | 9.70 ± 0.18 | 14.5 ± 0.6 | 0.4 ± 0.1 | 41 ± 14 | 0.28 ± 0.02 |

| Group | Number of Animals | Al.P (U/l) | LAP (U/l) | LDH (U/l) | GOT (U/l) | GPT (U/l) | GPK (U/l) | Albumin (g %) | A/G ratio |
|---|---|---|---|---|---|---|---|---|---|
| 1M | 5 | 198 ± 31 | 20 ± 1 | 111 ± 27 | 57 ± 6 | 12 ± 2 | 51 ± 10 | 3.44 ± 0.10 | 1.65 ± 0.07 |
| 2M | 4 | 194 ± 32 | 20 ± 1 | 86 ± 22 | 57 ± 6 | 13 ± 1 | 44 ± 5 | 3.43 ± 0.05 | 1.65 ± 0.05 |
| 3M | 5 | 149 ± 21 | 19 ± 1 | 99 ± 18 | 64 ± 9 | 14 ± 1 | 52 ± 9 | 3.47 ± 0.13 | 1.73 ± 0.07 |

TABLE 11

Histological findings in rat treated with Compound 18 for 2 weeks

| Compound Dose of Compound 18 (mg/kg/day) | Control | | | | | Compound 18 100 | | | | | Compound 18 300 | | | | |
|---|---|---|---|---|---|---|---|---|---|---|---|---|---|---|---|
| Rat number | 1 | 2 | 3 | 4 | 5 | 6* | 7 | 8 | 9 | 10 | 11 | 12 | 13 | 14 | 15 |
| Spleen | | | | | | | | | | | | | | | |
| Widening of red pulp | − | − | − | − | − | / | − | − | − | − | − | + | + | − | − |
| Congestion (dilatation of sinus) | − | − | − | − | − | / | − | − | − | − | − | − | − | − | − |
| Extramedullary hematopoiesis | + | + | + | + | + | / | + | + | + | + | + | + | ++ | + | + |
| Atrophy of white pulp | − | − | − | − | − | / | − | − | − | − | − | + | − | − | − |
| Liver | | | | | | | | | | | | | | | |
| Parenchymal cell altration | − | − | − | − | − | / | − | − | − | − | − | − | − | − | − |
| Kidney | | | | | | | | | | | | | | | |
| Dilatation of pelvis | +++ | − | − | ++ | − | / | − | − | ++ | + | − | + | − | − | − |
| Heart | | | | | | | | | | | | | | | |
| Cardiac cell alteration | − | − | − | − | − | / | − | − | − | − | − | − | − | − | − |
| Lung | | | | | | | | | | | | | | | |
| Alteration | − | − | − | − | − | / | − | − | − | − | − | − | − | − | − |
| Bone marrow | | | | | | | | | | | | | | | |
| Proliferation of erythroblast | − | − | − | − | − | / | − | − | − | − | − | − | − | − | − |

The scores indicate −: negative, +: mild, ++: moderate, +++: severe
*: The rat (No. 6) died of adminstration error during the experiment.
Male Wistar rats at 5 weeks of aged were used. They received oral admistration of Compound 18 for 2 weeks.
Control rats received 5% gum arabic solution at 10 ml per kilogram body weight.

with water and dried, and the solvent was evaporated off. The residue was purified with silica gel column chromatography (CHCl$_3$-MeOH (9:1)) and recrystalized from ethyl acetate-isopropyl ether, to give 8.0 g (77%) of 4-(3-pyridyl)-4-oxobutanol. m.p. 36°-37° C.

In a similar way, 5-(3-pyridyl)-5-oxopentanol (71%) and 6-(3-pyridyl)-6-oxohexanol (57%) were prepared from δ-valerolactone and from ε-caprolactone, respectively.

REFERENCE EXAMPLE 2

A solution of 12.5 g (69.8 mmol) of the alcohol derivative prepared in Reference Example 1 and 12.6 ml (90.7 mmol) of triethylamine in 100 ml of dimethylformamide were cooled with ice, to which 9.1 g (83.3 mmol) of trimethylchlorosilane was slowly added dropwise with stirring. The mixture was stirred for 30 minutes after completion of the addition and diluted with water, from which the product was extracted with ethyl acetate. The extract was washed with water and dried, and the solvent was evaporated off. The residue was distilled under reduced pressure, to give 13.4 g (76.4%) of 1-(3-pyridyl)-4-trimethysilyloxybutan-1-one (b.p. (1 mm) 126°-130° C.)

In a similar way, 1-(3-pyridyl)-5-trimethylsilyloxypentan-1-one (b.p.(1 mm) 134°-138° C.) and 1-(3-pyridyl)-6-trimethylsilyloxyhexan-1one (b.p. (1 mm) 140°-143° C.) were prepared.

REFERENCE EXAMPLE 3

A Grignard reagent was prepared from 7.73 g (29.8 mmol) of 1-bromo-2,5-dimethoxy-3,4,6-trimethoxybenzene, 700 mg (28.8 mmol) of magnesium, and 50 ml of tetrahydrofuran at 65° C., and the resultant solution was cooled to 0° C., to which the solution of 6.0 g (23.9 mmol) of the silyl ether derivative prepared in Reference Example 2 in 10 ml of tetrahydrofuran was added dropwise with stirring. The mixture was mixed at room temperature for 1 hour after completion of the addition, to which water was added and extracted with ethyl acetate. The extract was washed with water and dried (MgSO$_4$), and the solvent was evaporated off. To the residue ethanol (50 ml) and 2N hydrochloric acid (10 ml) were added and stirred for 1 hour. The reaction mixture was concentrated under reduced pressure and neutralized with sodium hydrogen carbonate, from which the product was extracted with ethyl acetate. The extract was washed with water and dried, and the solvent was evaporated off. The residue was dissolved in 80 ml of acetic acid, to which 15 ml of sulfuric acid was added and stirred at 80° C. for 30 minutes. After cooling followed by careful addition of 60 g of sodium hydrogen carbonate, the mixture was diluted with water, from which the product was extracted with ethyl acetate. The extract was washed with an aqueous solution of sodium hydrogen carbonate and then with water, and dried (MgSO$_4$), from which the solvent was evapporated off. The residue was purified with silica gel column chromatography (CHCl$_3$-EtOAc (1:1)), to give 4.09 g (43.8%) of 1-acetoxy-4-(2,5-dimethoxy-3,4,6-trimethylphenyl)-4-(3-pyridyl)-3-butene (an oil).

In a similar way, 1-acetoxy-5-(2,5-dimethoxy-3,4,6-trimethylphenyl)-5-(3-pyridyl)-4-pentene and 1-acetoxy-6-(2,5-dimethoxy-3,4,6-trimethylphenyl)-6-(3-pyridyl)-5-hexene were prepared.

REFERENCE EXAMPLE 4

A solution of 1.0 g (2.7 mmol) of the butene derivative prepared in Reference Example 3 in 10 ml of acetic acid was subjected to a catalytic reduction at 80° C. in the presence of 0.4 g of 5% palladium-carbon catalyst. After completion of the reaction, the catalyst was removed by filtration, and the filtrate was concentrated under reduced pressure. The residue was dissolved in ethyl acetate, washed with an aqueous solution of sodium hydrogen carbonate and then with water, and dried, from which the solvent was evaporated off. The residue was purified with silica gel column (ethyl acetate), to give 750 mg (74.6%) of 1-acetoxy-4-(2,5-dimethoxy-3,4,6-trimethylphenyl)-4-(3-pyridyl)butane (an oil).

In a similar way 1-acetoxy-6-(2,5-dimethoxy-3,4,6-trimethylphenyl)-6-(3-pyridyl)hexane and 1-acetoxy-5-(2,5-dimethoxy-3,4,6-trimethylphenyl)-5-(3-pyridyl)-pentane were prepared.

REFERENCE EXAMPLE 5

To a solution of 0.7 g (1.88 mmol) of the butane derivative prepared in Reference Example 4 in 3 ml of methanol, a solution of 0.3 g (7.50 mmol) of sodium hydroxide in 3 ml of water was added and stirred at room temperature for 30 minutes, to which water was added. The product was extracted with ethyl acetate, and the extract was washed with water, dried, and concentrated. The residue was purified with a silica gel short column (ethyl acetate), to give 0.5 g (80.5%) of 4-(2,5-dimethoxy-3,4,6-trimethylphenyl)-4-(3-pyridyl)-1-butanol (an oil).

In a similar way 5-(2,5-dimethoxy-3,4,6-trimethylphenyl)-5 -(3-pyridyl)-1-pentanol (m.p. 99°-100° C.) and 6-(2,5-dimethoxy-3,4,6-trimethylphenyl)-6-(3-pyridyl)-1-hexanol (m.p. 90°-91° C.) were prepared.

REFERENCE EXAMPLE 6

A solution of 10.0 g (63.3 mmol) of 3-bromopyridine in 100 ml of ether was cooled to −78° C., to which 40 ml of 1.6M (64 mmol) n-butyllithium hexane solution was added dropwise. The mixture was stirred for 15 minutes after completion of the addition, to which a solution of 7.52 g (67.7 mmol) of heptanitrile in 15 ml of ether was added dropwise and stirred at −78° C. to room temperature further for 1 hour. To the reaction mixture an aqueous solution of ammonium chloride was added, from which the product was extracted with ethyl acetate. The extract was washed with water and dried, and the solvent was evaporated off. The residue was purified with silica gel column chromatography (eluted with isopropyl ether), to give 3.9 g (36%) of 3-heptanoylpyridine (an oil).

In a similar way 3-propionylpyridine and 3-pentanoylpyridine were prepared by the reaction with propionitrile and with valeronitrile, respectively.

REFERENCE EXAMPLE 7

A Grignard reagent was prepared from 693 mg (28.3 g atom) of magnesium, 7.6 g (29.3 mmol) of 1-bromo-2,5-dimethoxy-3,4,6-trimethylbenzene and tetrahydrofuran at 65° C. and cooled to 0° C., to which a solution of 3.75 g (21.9 mmol) of 3-heptanoylpyridine in 10 ml of tetrahydrofuran was added dropwise. After completion of the addition, the reaction mixture was stirred at room temperature for 1 hour, to which water was added and extracted with ethyl acetate. The extract was washed with water, dried and concentrated. The residue was purified with silica gel column chromatography (isopropyl ether) and recrystallized from hexane, to give 3.2 g (39%) of 1-(2,5-dimethoxy-3,4,6-trimethylphenyl)-1-(3-pyridyl)heptanol. m.p. 109°-110° C.

In a similar way 1-(2,5-dimethoxy-3,4,6-trimethylphenyl)-1-(3-pyridyl)propanol and 1-(2,5-dimethoxy-3,4,6-trimethylphenyl)-1-(3-pyridyl)pentanol were prepared.

REFERENCE EXAMPLE 8

To a solution of 2.5 g (6.74 mmol) of the alcohol derivative prepared in Reference 7 in 20 ml of acetic acid, 2.5 ml of concentrated sulfuric acid was added and heated at 80° C. for 1 hour. After cooling, 6.8 g of potassium carbonate was added carefully, which was diluted with water and extracted with ethyl acetate. The extract was washed with water and with an aqueous solution of sodium hydrogen carbonate and dried, from which the solvent was evaporated off. Purification with a short column of silica gel (isopropyl ether) gave 2.2 g (92.5%) of 1-(2,5-dimethoxy-3,4,6-trimethylphenyl)-1-(3-pyridyl)-1-heptene.

REFERENCE EXAMPLE 9

The heptene derivative prepared in Reference Example 8, 1.2 g (3.4 mmol), was hydrogenated in 12 ml of acetic acid in the presence of 0.6 g of 5% Pd-carbon at 80° C. The reaction mixture was analyzed with TLC. After completion of the reaction, the catalyst was removed by filtration, and the filtrate was concentrated, to which ethyl acetate was added and washed with a saturated aqueous solution of sodium hydrogen carbonate. The organic phase was dried from which the solvent was evaporated. The residue was purified with silica gel column chromatography (isopropyl ether-hexane (2:1)), to give 1.1 g (91.2%) of 1-(2,5-dimethoxy-3,4,6-trimethylphenyl)-1-(3-pyridyl)heptane (an oil).

In a similar way 1-(2,5-dimethoxy-3,4,6-trimethylphenyl)-1-(3-pyridyl)propane and 1-(2,5-dimethoxy-3,4,6-trimethylphenyl)-1-(3-pyridyl)pentane were prepared.

REFERENCE EXAMPLE 10

The solution of 525 mg (1.6 mmol) of the butanol derivative prepared in Reference Example 5 and 0.33 ml (2.4 mmol) of triethylamine in 3.5 ml of dichloromethane was cooled to 0° C., to which 0.15 ml (1.94 mmol) of methanesulfonyl chloride was added with stirring. The reaction mixture was stirred at the same temperature for 30 minutes, to which water was added and the organic layer was separated while the water layer was extracted with dichloromethane and the extract was combined with the organic layer described above. The resultant organic layer was washed with water, dried, and concentrated. The residue was dissolved in 5 ml of dimethylsulfoxide, to which 148 mg (2.9 mmol) of sodium cyanide was added and stirred at 80° C. for 2 hours. To the reaction mixture water was added, from which the product was extracted with ethyl acetate. The extract was washed with water and dried, from which the solvent was evaporated off. The residue was purified with silica gel column chromatography, to give 445 mg (82.5%) of 4-cyano-1-(2,5-dimethoxy-3,4,6-trimethylphenyl)-1-(3-pyridyl)butane (an oil).

In a similar way, 5-cyano-1-(2,5-dimethoxy-3,4,6-trimethylphenyl)-1-(3-pyridyl)pentane(oil), 6-cyano-1-(2,5-dimethoxy-3,4,6-trimethylphenyl)-1-(3-pyridyl)hexane (oil) and 7-cyano-1-(2,5-dimethoxy-3,4,6-trimethylphenyl)-1-(3-pyridyl)heptane(oil) were prepared.

REFERENCE EXAMPLE 11

To a solution of 445 mg (1.32 mmol) of the cyano derivative prepared in Reference Example 10 in 3 ml of methanol, a solution of 1.5 g (37.5 mmol) of sodium hydroxide in 5 ml of water was added and refluxed by heating for 3 hours. The reaction mixture was cooled, diluted with water, neutralized with 2N hydrochloric acid, and extracted with ethyl acetate. The extract was washed with water, dried, and concentrated. The residue was purified with silica gel column chromatography (CHCl$_3$:MeOH (9:1)), to give 400 mg (85.1%) of 5-(2,5-dimethoxy-3,4,6-trimethylphenyl)-5-(3-pyridyl)pentanoic acid. m.p. 82°-84° C.

In a similar way, 6-(2,5-dimethoxy-3,4,6-trimethylphenyl)-6-(3-pyridyl)hexanoic acid (m.p. 183°-184° C.), 7-(2,5-dimethoxy-3,4,6-trimethylphenyl)-7-(3-pyridyl)heptanoic acid (an oil) and 8-(2,5-dimethyl-3,4,6-trimethylphenyl)-8-(3-pyridyl)octanoic acid (oil) were prepared.

REFERENCE EXAMPLE 12

A solution of 5.0 g (17.8 mmol) of 2-bromo-1,4-dimethoxy-3-methylnaphthalene in 30 ml of tetrahydrofuran was cooled to −78° C., to which 11.2 ml (17.9 mmol) of 1.6M n-butyllithium hexane solution was added dropwise, and stirred at the same temperature for 10 minutes after completion of the addition. Then 1.3 g (17.8 mmol) of dimethylformamide was added dropwise to the reaction mixture, and stirred at room temperature for 1 hour after completion of the addition. Water was added to the reaction mixture, from which the product was extracted with ethyl acetate. The extract was washed with water, dried, and concentrated. The residue was purified with silica gel column chromatography (hexane-isopropyl ether (8:2), and crystallized from hexane-isopropyl ether, to give 2.0 g (48.9%) of 2-formyl-1,4-dimethoxy-3-methylnaphthalene. m.p. 95°-96° C.

REFERENCE EXAMPLE 13

A solution of 1.0 g (2.82 mmol) of the heptene derivative prepared in Reference Example 8 in 20 ml of acetonitrile-water (1:1) was cooled with ice, to which a solution of 4.1 g (7.48 mmol) of cerium ammonium nitrate in 15 ml of acetonitrile-water (1:1) was added dropwise with stirring. The mixture was stirred at the same temperature for 30 minutes after completion of the addition, made weakly alkaline with an aqueous solution of sodium hydrogen carbonate, and extracted with ethyl acetate. The extract was washed with water and dried, and the solvent was evaporated off. The residue was separated with silica gel column chromatography (isopropyl ether):313 mg of (E)-1-(3,5,6-trimethylbenzoquinon-2-yl)-1-(3-pyridyl)heptene eluted ahead, and 395 mg of (Z)-1-(3,5,6-trimethylbenzoquinon-2-yl)-1-(3-pyridyl)heptene eluted later were obtained.

In a similar way (E), (Z)-7-(3,5,6-trimethylbenzoquinon-2-yl)-7-(3-pyridyl)heptenoic acid was prepared.

The physical data of the compounds described above are shown in Table 12.

TABLE 12

| Formula | Molecular formula physical properties | Nuclear magnetic resonance spectrum, δ value (ppm) in CDCl$_3$, TMS as internal standard |
|---|---|---|
| [Structure: 2,3,5-trimethyl-6-(1-(3-pyridyl)hept-1-enyl)-1,4-benzoquinone, E form*] | C$_{21}$H$_{25}$NO$_2$ oil | 0.83(3H, t, J=6.0Hz), 1.30(6H, m), 1.93(3H, s), 2.00(3H, s), 2.10(3H, s), 2.20(2H, m), 5.67(1H, t, J=6.0Hz), 7.21(1H, dd, J=7.5&4.5Hz), 7.53(1H, dt, J=7.5&1.5Hz), 8.47(2H, m) |
| [Structure: Z form**] | C$_{21}$H$_{25}$NO$_2$ oil | 0.87(3H, t, J=6.0Hz), 1.30(6H, m), 1.93(3H, s), 2.00(3H, s), 2.10(3H, s), 2.20(2H, m), 6.23(1H, t, J=6.0Hz), 7.20(1H, dd, J=7.5&4.5Hz), 7.52(1H, dt, J=7.5&1.5Hz), 8.40(1H, dd, J=4.5&1.5Hz), 8.47(1H, d, J=1.5Hz) |
| [Structure: COOH-terminated analog, (E + Z)***] | C$_{21}$H$_{23}$NO$_4$ oil | 1.60(4H, m), 1.97(23H, s), 2.03(3H, s), 2.13(3H, s), 2.0–2.50(4H, m),5.70(0.5H, t, J=7.5Hz), 6.27(0.5H, t, J=7.5Hz), 7.25(1H, m), 7.55(1H, m), 8.50(3H, m) |

*E means the isomer where the pyridine nucleus on the one carbon and hydrogen atom on the other carbon are on the same direction in the tri-substituted olefin bond.
**Z means the isomers where they are on the opposite directions to each other.
***E + Z means a mixture of E and Z.

REFERENCE EXAMPLE 14

1,4-Dimethoxy-2,3,5-trimethylbenzene, 9.00 g (50 mmole), was dissolved in CH$_2$Cl$_2$(60 ml) and stirred with ice-cooling. After addition of 14.4 g (50×2.5 mmole) of dichloromethyl methyl ether, 13.8 ml (50×2.5 mmole) of titanium tetrachloride dissolved in CH$_2$Cl$_2$ (30 ml) was added dropwise over 15 minutes. After stirring for further 15 minutes with ice-cooling, the ice bath was removed and the mixture was stirred at room temperature for 4 hours. The reaction mixture was poured into crashed ice (about 200 g) and stirred vigorously for 30 minutes. The CH$_2$Cl$_2$layer was washed with water (3 times), and dried (MgSO$_4$), from which CH$_2$Cl$_2$ was evaporated off. The residue was recrystallized from isopropyl ether/hexane (1:1), to give 6.18 g of 2,5-dimethoxy-3,4,6-trimethylbenzaldehyde. The mother liquor was concentrated, and the residue was purified with silica gel (60 g) column chromatography (eluted with isopropyl ether), to give 3.70 g of 2,5-dimethoxy-3,4,6-trimethylbenzaldehyde. Yield 9.88 g (95%), m.p. 85°–86° C.

To a solution of 20 g (96 mmol) of 2,5-dimethoxy-3,4,6-trimethylbenzaldehyde in 200 ml of ethanol, 1.8 g (47.6 mmol) of sodium boronhydride was added and stirred for 30 minutes. To the reaction mixture saline was added, and the product was extracted with ethyl acetate. The extract was washed with water and dried, from which the solvent was evaporated off under reduced pressure. The residue was crystallized from isopropyl ether, to give 18.6 g (92.1%) of 2,5-dimethoxy-3,4,6-trimethylbenzylalcohol. m.p. 121°–122° C.

A solution of 16.5 g (78.5 mmol) of 2,5-dimethoxy-3,4,6-trimethylbenzylalcohol in 90 ml of tetrahydrofuran was cooled to 0° C., to which 14.2 g (52.5 mmol) of phosphorus tribromide was added with stirring. After stirring at the same temperature for 30 minutes, the reaction mixture was diluted with water and extracted with isopropyl ether. The extract was washed with a saturated aqueous solution of sodium hydrogen carbonate and dried, from which the solvent was evaporated off. The residue was crystallized from methanol, to give 17.2 g (80.0%) of 2,5-dimethoxy-3,4,6-trimethylbenzyl bromide. m.p. 71°–72° C.

A solution of 15.5 g (98.1 mmol) of 3-bromopyridine in 200 ml of ethyl ether was cooled to −78° C., to which 61.3 ml (98.1 mmol) of n-butyllithium (1.6M hexane solution) was added dropwise. For 20 minutes after completion of the addition, the mixture was stirred at the same temperature, and then a solution of 26.8 g (98.1 mmol) of 2,5-dimethoxy-3,4,6-trimethylbenzyl bromide in 100 ml of ethyl ether was added dropwise.

After stirring at −78° C. to room temperature for 1 hour, the reaction mixture was diluted with water and extracted with ethyl acetate. Then the extract was extracted reversely with 2N-hydrochloric acid, and the water layer was made weakly alkaline with a saturated aqueous solution of sodium hydrogen carbonate and extracted with ethyl acetate. The extract was washed with water, dried, and concentrated. The residue was purified with silica gel column chromatography (ethyl acetate), to give 22.8 g (85.8%) of 3-(2,5-dimethoxy-3,4,6-trimethylbenzyl)pyridine.

In a similar way, using 2-formyl-1,4-dimethoxy-3-methylnaphthalene as the starting substance, 3-[(2-(1,4-dimethoxy-3-methylnaphthyl))methyl]pyridine was synthesized via [2-(1,4-dimethoxy-3-methylnaphthyl)]methanol (m.p. 122°–123° C.) and [2-(1,4-dimethoxy-3-methylnaphthyl)]methyl bromide (m.p. 79°–80° C.).

REFERENCE EXAMPLE 15

To a solution of 499 mg (7.33 mmol) of imidazole and 2.0 g (7.33 mmol) of 2,5-dimethoxy-3,4,6-trimethylbenzyl bromide in 12 ml of dimethylformamide, 1.2 ml of triethylamine was added and stirred at room temperature for 1 hour. The reaction mixture was diluted with water and extracted with ethyl acetate. The extract was washed with water and dried, from which the solvent was evaporated off. The residue was purified with silica gel column chromatography (chloroform-methanol(1:1)) and recrystallized from isopropyl ether, to give 0.9 g (47.3%) of 1-(2,5-dimethoxy-3,4,6-trimethylbenzyl)imidazole. m.p. 82°–83° C.

REFERENCE EXAMPLE 16

To a stirred tetrahydrofurane solution (40 ml) of 7-(2,5-dimethoxy-3,4,6-trimethylphenyl)-7-(3-pyridyl)-heptanoic acid (3.0, 7.8 mmol) prepared in the Reference Example 11 was added lithium aluminum hydride (450 mg, 11.9 mmol) under ice-cooling. The reaction mixture was allowed to rise to room temperature and stirred for 30 min. After that water was carefully added to the reaction mixture and the product was extracted with ethylacetate. The extract was washed with water, dried, and evaporated in vacuo to yield 7-(2,5-dimethoxy-3,4,6-trimethylphenyl)-7-(3-pyridyl)heptanol (2.3 g, 79.6%) as, an oil, after chromatography of the crude product on silica gel.

What is claimed is:

1. A compound of the formula:

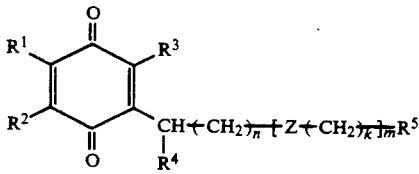

$R^1$ and $R^2$ are the same or different and are methyl or methoxy, or $R^1$ and $R^2$ bind together to form —CH=CH—CH=CH—;

$R^3$ is methyl $R^4$ is thiazolyl or imidazolyl which may be substituted by 1 to 3 substituents selected from the group consisting of alkyl of 1 to 3 carbon atoms, phenyl, p-tolyl, m-tolyl, pyridyl and 3-pyridylmethyl;

$R^5$ is hydrogen, methyl, hydroxymethyl, methoxymethyl, acetoxymethyl, nitroxymethyl, carbamoyloxymethyl or a carboxyl group which may be esterified with an alkyl having 1 to 3 carbon atoms or amidated to form hydroxyaminocarbonyl, morpholinocarbonyl, piperidinocarbonyl or carboxamide of the formula:

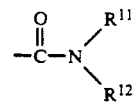

wherein $R^{11}$ and $R^{12}$ individually represent hydrogen, $C_1$–$C_7$ alkyl, phenyl hydroxyl, methoxy or chlorine or naphthyl, n is 0 or an integer from 1 through 12;

m is 0 or an integer from 1 through 3;

k is 0 or an integer from 1 through 7

Z is

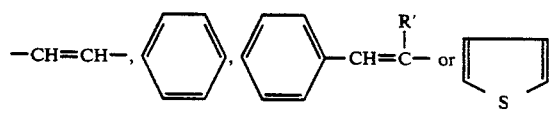

wherein R' is hydrogen or methyl, providing that, when m is 2 or 3, k may vary appropriately in the repeating unit shown in [].

2. A compound as claimed in claim 1, wherein m is 0 or 1.

3. A compound as claimed in claim 1, wherein m is 1 and k is 0 or an integer from 1 through 3.

4. A compound as claimed in claim 1, wherein $R^4$ is imidazolyl which may be substituted by 1 to 3 substituents selected from the group consisting of alkyl of 1 to 3 carbon atoms, phenyl, p-tolyl, m-tolyl, pyridyl and 3-pyridylmethyl.

5. A compound as claimed in claim 1, wherein $R^1$ and $R^2$ is methyl or $R^1$ and $R^2$ bind together to form —CH=CH—CH=CH—.

6. A compound as claimed in claim 1, wherein $R^5$ is hydroxymethyl, methoxymethyl, acetoxymethyl, nitroxymethyl or carbamoyloxymethyl.

7. A compound as claimed in claim 1, wherein $R^5$ is a carboxyl group which may be esterified or amidated.

8. A compound as claimed in claim 7, wherein the carboxyl group which may be esterified or amidated is carboxyl, an alkoxycarbonyl wherein the alkyl has 1 to 3 carbon atoms, aminocarbonyl, a mono- or dialkylaminocarbonyl wherein the alkyl has 1 to 3 carbon atoms, phenylaminocarbonyl, diphenylaminocarbonyl.

9. A compound as claimed in claim 1, wherein the compound is 2-[(1-imidazolyl)methyl]-3,5,6-trimethyl-1,4-benzoquinone hydrochloride.

10. A pharmaceutical composition for the treatment of disease due to dysfunction of heart, brain, lung or kidney which comprises a pharmaceutically effective amount of a compound according to claim 1 or the corresponding hydroquinone derivative thereof and pharmaceutically acceptable carrier therefor.

11. A method for the treatment of a disease due to dysfunction of heart, brain, lung or kidney which comprises administering to a mammal a pharmaceutically effective amount of a compound according to claim 1 or the corresponding hydroquinone derivative thereof.

* * * * *

UNITED STATES PATENT AND TRADEMARK OFFICE
CERTIFICATE OF CORRECTION

PATENT NO. : 5,229,385
DATED : July 20, 1993
INVENTOR(S) : SHINJI TERAO and KOHEI NISHIKAWA It is certified that error appears in the above-identified patent and that said Letters Patent is hereby corrected as shown below:

Column 34, line 2, change "3" to —4—;

line 14, after "phenyl" insert —which may be substituted with—;

line 15, after "chlorine" insert a comma (,).

Signed and Sealed this

Eighteenth Day of April, 1995

*Attest:*

BRUCE LEHMAN

*Attesting Officer*      *Commissioner of Patents and Trademarks*